US009370496B2

(12) United States Patent
Miller

(10) Patent No.: US 9,370,496 B2
(45) Date of Patent: Jun. 21, 2016

(54) TREATMENT OF LEBER'S HEREDITARY OPTIC NEUROPATHY AND DOMINANT OPTIC ATROPHY WITH TOCOTRIENOL QUINONES

(71) Applicant: Edison Pharmaceuticals, Inc., Mountain View, CA (US)

(72) Inventor: Guy M. Miller, Monte Sereno, CA (US)

(73) Assignee: EDISON PHARMACEUTICALS, INC., Mountain View, CA (US)

( * ) Notice: Subject to any disclaimer, the term of this patent is extended or adjusted under 35 U.S.C. 154(b) by 0 days.

(21) Appl. No.: 13/859,592

(22) Filed: Apr. 9, 2013

(65) Prior Publication Data

US 2014/0039065 A1 Feb. 6, 2014

Related U.S. Application Data

(63) Continuation of application No. 12/768,565, filed on Apr. 27, 2010, now abandoned.

(60) Provisional application No. 61/214,795, filed on Apr. 28, 2009, provisional application No. 61/318,733, filed on Mar. 29, 2010.

(51) Int. Cl.
*A61K 31/05* (2006.01)
*A61K 31/122* (2006.01)
*A61K 9/00* (2006.01)

(52) U.S. Cl.
CPC ............. *A61K 31/122* (2013.01); *A61K 9/0048* (2013.01); *A61K 31/05* (2013.01)

(58) Field of Classification Search
USPC ........................................................ 514/690
See application file for complete search history.

(56) References Cited

U.S. PATENT DOCUMENTS

| | | | |
|---|---|---|---|
| 4,804,539 A | 2/1989 | Guo et al. | |
| 4,883,658 A | 11/1989 | Holly | |
| 4,914,088 A | 4/1990 | Glonek et al. | |
| 5,075,104 A | 12/1991 | Gressel et al. | |
| 5,157,132 A | 10/1992 | Tan et al. | |
| 5,190,618 A | 3/1993 | Top et al. | |
| 5,278,151 A | 1/1994 | Korb et al. | |
| 5,294,607 A | 3/1994 | Glonek et al. | |
| 5,318,993 A | 6/1994 | Pearce | |
| 5,371,108 A | 12/1994 | Korb et al. | |
| 5,578,586 A | 11/1996 | Glonek et al. | |
| 5,801,159 A | 9/1998 | Miller et al. | |
| 5,874,461 A | 2/1999 | De Chaffoy de Courcelles et al. | |
| 5,886,030 A | 3/1999 | Maniar | |
| 6,232,060 B1 | 5/2001 | Miller et al. | |
| 6,239,171 B1 | 5/2001 | Lane et al. | |
| 6,395,915 B1 | 5/2002 | Bellafiore et al. | |
| 6,426,362 B1 | 7/2002 | Miller et al. | |
| 6,528,042 B1 | 3/2003 | Brown et al. | |
| 6,608,196 B2 | 8/2003 | Wang et al. | |
| 6,653,346 B1 | 11/2003 | Wang et al. | |
| 6,656,358 B2 | 12/2003 | May et al. | |
| 6,838,104 B2 | 1/2005 | Jacobs | |
| 7,034,054 B2 | 4/2006 | Miller et al. | |
| 7,038,067 B2 | 5/2006 | Couladouros et al. | |
| 7,078,541 B2 | 7/2006 | Boddupalli et al. | |
| 7,119,117 B2 | 10/2006 | Beinlich et al. | |
| 7,393,662 B2 | 7/2008 | Heavner et al. | |
| 7,432,305 B2 | 10/2008 | Miller et al. | |
| 7,470,798 B2 | 12/2008 | Wang et al. | |
| 7,491,312 B2 | 2/2009 | Gilat et al. | |
| 7,514,461 B2 | 4/2009 | Wang et al. | |
| 7,718,176 B2 | 5/2010 | Heavner et al. | |
| 7,875,607 B2 | 1/2011 | Wang et al. | |
| 7,968,746 B2 | 6/2011 | Jankowski et al. | |
| 8,044,097 B2 | 10/2011 | Wang et al. | |
| 8,106,223 B2 | 1/2012 | Wesson et al. | |
| 8,314,153 B2 | 11/2012 | Miller et al. | |
| 8,519,001 B2 | 8/2013 | Jankowski et al. | |
| 8,575,369 B2 | 11/2013 | Wesson et al. | |
| 8,653,144 B2 | 2/2014 | Miller et al. | |
| 8,716,486 B2 | 5/2014 | Hinman et al. | |
| 8,716,527 B2 | 5/2014 | Hinman et al. | |
| 8,791,155 B2 | 7/2014 | Wang et al. | |
| 2002/0132845 A1 | 9/2002 | Miller et al. | |
| 2003/0022818 A1 | 1/2003 | Miller et al. | |
| 2003/0144219 A1 | 7/2003 | Phinney et al. | |
| 2005/0049227 A1 | 3/2005 | Old et al. | |
| 2005/0065099 A1 | 3/2005 | Walkinshaw et al. | |
| 2005/0074447 A1 | 4/2005 | Papas et al. | |
| 2006/0241174 A1 | 10/2006 | Mueller et al. | |
| 2006/0281809 A1 | 12/2006 | Miller et al. | |
| 2007/0066541 A1 | 3/2007 | Hughes et al. | |
| 2007/0225261 A1* | 9/2007 | Miller et al. ................... 514/125 |
| 2009/0060981 A1 | 3/2009 | Chauhan | |
| 2009/0162890 A1 | 6/2009 | Gilat et al. | |
| 2009/0163529 A1 | 6/2009 | Gilat et al. | |
| 2009/0291092 A1 | 11/2009 | Miller et al. | |
| 2010/0010100 A1 | 1/2010 | Hinman et al. | |

(Continued)

FOREIGN PATENT DOCUMENTS

EP 1 378 753 A1 1/2004
EP 1 611 879 A1 1/2006

(Continued)

OTHER PUBLICATIONS

Brown (Leber's Hereditary Optic Neuropathy: a Model for Mitochondrial Neurodegenerative Diseases, the FASEB Journal, vol. 6, Jul. 1992, pp. 2792-2799).*

(Continued)

*Primary Examiner* — Kathrien Cruz

(74) *Attorney, Agent, or Firm* — Squire Patton Boggs (US) LLP

(57) ABSTRACT

The present invention relates to methods of treating Leber's hereditary optic neuropathy and dominant optic atrophy with tocotrienol quinones, including alpha-tocotrienol quinone, in order to alleviate symptoms of the disease.

16 Claims, 9 Drawing Sheets

(56) References Cited

U.S. PATENT DOCUMENTS

| | | |
|---|---|---|
| 2010/0029784 A1 | 2/2010 | Hinman et al. |
| 2010/0056429 A1 | 3/2010 | Miller et al. |
| 2010/0093845 A1 | 4/2010 | Wong et al. |
| 2010/0222436 A1 | 9/2010 | Miller et al. |
| 2010/0249032 A1 | 9/2010 | Heavner et al. |
| 2010/0266591 A1 | 10/2010 | Bugelski et al. |
| 2010/0273892 A1 | 10/2010 | Miller et al. |
| 2010/0273894 A1 | 10/2010 | Miller |
| 2011/0046156 A1 | 2/2011 | Miller |
| 2011/0046219 A1 | 2/2011 | Hinman et al. |
| 2011/0142834 A1 | 6/2011 | Miller |
| 2011/0172312 A1 | 7/2011 | Miller et al. |
| 2011/0207828 A1 | 8/2011 | Miller et al. |
| 2011/0269776 A1 | 11/2011 | Miller |
| 2012/0101169 A1 | 4/2012 | Hawi |
| 2012/0122969 A1 | 5/2012 | Miller |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |
| 2013/0267538 A1 | 10/2013 | Walkinshaw et al. |
| 2013/0289034 A1 | 10/2013 | Jankowski et al. |
| 2013/0345312 A1 | 12/2013 | Jankowski et al. |
| 2014/0031432 A1 | 1/2014 | Jankowski et al. |
| 2014/0031433 A1 | 1/2014 | Miller et al. |
| 2014/0206772 A1 | 7/2014 | Miller et al. |
| 2014/0221674 A1 | 8/2014 | Wesson et al. |
| 2014/0243424 A1 | 8/2014 | Mollard et al. |
| 2014/0249160 A1 | 9/2014 | Miller et al. |
| 2014/0249332 A1 | 9/2014 | Mollard et al. |
| 2014/0256830 A1 | 9/2014 | Hinman et al. |
| 2014/0275045 A1 | 9/2014 | Hinman et al. |
| 2014/0275054 A1 | 9/2014 | Hinman et al. |

FOREIGN PATENT DOCUMENTS

| | | |
|---|---|---|
| JP | 48-75564 A | 10/1973 |
| JP | 49-88862 A | 8/1974 |
| JP | 63-063674 A | 3/1988 |
| JP | 1-233278 A | 9/1989 |
| JP | 2007-529218 A | 10/2007 |
| JP | 2008-542389 A | 11/2008 |
| JP | 2009-527567 A | 7/2009 |
| WO | WO-99/38860 A1 | 8/1999 |
| WO | WO-00/78296 A2 | 12/2000 |
| WO | WO-00/78296 A3 | 12/2000 |
| WO | WO-02/47680 A2 | 6/2002 |
| WO | WO-02/47680 A3 | 6/2002 |
| WO | WO-02/47680 A9 | 6/2002 |
| WO | WO-02/50054 A2 | 6/2002 |
| WO | WO-02/50054 A3 | 6/2002 |
| WO | WO-03/064403 A1 | 8/2003 |
| WO | WO-2004/003565 A2 | 1/2004 |
| WO | WO-2004/003565 A3 | 1/2004 |
| WO | WO-2005/090602 A2 | 9/2005 |
| WO | WO-2005/090602 A3 | 9/2005 |
| WO | WO-2006/130775 A2 | 12/2006 |
| WO | WO-2006-130775 A3 | 12/2006 |
| WO | WO-2007/100652 A2 | 9/2007 |
| WO | WO-2007/100652 A3 | 9/2007 |
| WO | WO-2008/157747 A1 | 12/2008 |
| WO | WO-2009/023877 A2 | 2/2009 |
| WO | WO-2009/023877 A3 | 2/2009 |
| WO | WO-2011/025785 A1 | 3/2011 |
| WO | WO-2011/041452 A2 | 4/2011 |
| WO | WO-2011/041452 A3 | 4/2011 |
| WO | WO-2011/113018 A1 | 9/2011 |
| WO | WO-2011/126998 A1 | 10/2011 |
| WO | WO-2011/137126 A1 | 11/2011 |
| WO | WO-2012/019029 A2 | 2/2012 |
| WO | WO-2012/019029 A3 | 2/2012 |
| WO | WO-2012/019032 A1 | 2/2012 |
| WO | WO-2012/154613 A1 | 11/2012 |
| WO | WO-2012/170773 A1 | 12/2012 |
| WO | WO-2012/174286 A1 | 12/2012 |
| WO | WO-2013/006736 A1 | 1/2013 |
| WO | WO-2013/006737 A1 | 1/2013 |
| WO | WO-2013/013078 A1 | 1/2013 |
| WO | WO-2014/039862 A1 | 3/2014 |
| WO | WO-2014/039917 A1 | 3/2014 |
| WO | WO/2014/194292 A1 | 12/2014 |

OTHER PUBLICATIONS

Kwong (The role of mitcochondris in inherited neurodegenerative diseases, Journal of Neurochemistry, 2006, 97, pp. 1659-1675).*

Packer et al. (Symposium: Molecular Mechanisms of Protective Effects of Vitamin E in Atherosclerosis, "Molecular Aspects of a-Tocotrienol Antioxidant Action and Cell Signalling". The Journal of Nutrition, 2001, 396S-373S).*

Alexander, C. et al. (Oct. 2000). "OPA1, Encoding a Dynamin-Related GTPase, is Mutated in Autosomal Dominant Optic Atrophy Linked to Chromosome 3q28," *Nature Genetics* 26(2):211-215.

Biousse, V. et al. (Feb. 2003). "Neuro-Ophthalmology of Mitochondrial Diseases," *Current Opinion in Neurology* 16(1):35-43.

Bremner, F.D. (2004). "Pupil Assessment in Optic Nerve Disorders," *Eye* 18:1175-1181.

Carelli, V. (2002). "Optic Nerve Degeneration and Mitochondrial Dysfunction: Genetic and Acquired Optic Neuropathies," *Neurochemistry International* 40:573-584.

Carelli, V. et al. (2009, e-pub. Mar. 5, 2009). "Retinal Ganglion Cell Neurodegeneration in Mitochondrial Inherited Disorders," *Biochimica et Biophysica Acta* 1787:518-528.

Csaky, K.G. (Mar./Apr. 2007). "New Developments in the Trans-scleral Delivery of Ophthalmic Agents," *Retina Today*, pp. 32-35.

Delettre, C. et al. (Oct. 2000). "Nuclear Gene OPA1, Encoding a Mitochondrial Dynamin-Related Protein, is Mutated in Dominant Optic Atrophy," *Nature Genetics* 26(2):207-210.

Ghate, D. et al. (May 2007). "Pharmacokinetics of Intraocular Drug Delivery by Periocular Injections Using Ocular Fluorophotometry," *Investigative Ophthalmology and Visual Science* 48(5):2230-2237.

Gouw, L.G. et al. (May 1995). "Retinal Degeneration Characterizes a Spinocerebellar Ataxia Mapping to Chromosome 3p," *Nature Genetics* 10:89-93.

Grönlund, M.A. et al. (2010). "Ophthalmological Findings in Children and Young Adults with Genetically Verified Mitochondrial Disease," *Br. J. Ophthalmol.* 94:121-127.

Gubskii, Y.I. et al. (2008). "Antioxidant and Membranotropic Effects of Monochromanes and Trimethylphenol Derivatives in Vitro," *Ukrains'kii Biokhimichnii Zhurnal* 80(6):79-85, Chemical Abstract Only, CAPLUS Abstract No. 2009:267923.

Gupta, S.N. et al. (Jan. 15, 2008, e-pub. Aug. 27, 2007). "Spinocerebellar Ataxia Type 7 Mimicking Kearns-Sayre Syndrome: A Clinical Diagnosis is Desirable," *Journal of Neurological Sciences* 264:173-176.

Haas, R.H. et al. (May 2008). "The In-Depth Evaluation of Suspected Mitochondrial Disease: The Mitochondrial Medicine Society's Committee on Diagnosis," *Mol. Genet. Metab.* 94(1):16-37, thirty-two pages.

Huang, C.-C. et al. (Mar. 2002). "Rapid Visual Recovery After Coenzyme Q10 Treatment of Leber Hereditary Optic Neuropathy," *The Journal of Neuro-Opthalmology* 22(1):66-67.

Hudson, G. et al. (Jul. 2008). "Leber Hereditary Optic Neuropathy," *Expert Opinion on Medical Diagnostics* 2(7):789-799.

Jarrett, S.G. et al. (2008). "Mitochondrial DNA Damage and Its Potential Role in Retinal Degeneration," *Progress in Retinal and Eye Research* 27:596-607.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (Oct. 2003, e-pub. Aug. 15, 2003). "Mitochondria-Targeted Antioxidants Protect Friedreich Ataxia Fibroblasts from Endogenous Oxidative Stress More Effectively Than Untargeted Antioxidants" *The FASEB Journal* 17(13):1972-1974.

Kabbe, H.J. et al. (1978). "Eine Neue Synthese von 3,4-Dehydro-α-Tocotrienol und Vitamin-E," *Synthesis* 888-889. (Translation of

(56) References Cited

OTHER PUBLICATIONS

Abstract only: Chemical Abstract CAPLUS Abstract No. 1979:168774, two pages.).
Kajiwara, M. et al. (1980). "Studies on Tocopherols II[1]. Convenient Synthesis of Tocopherols," *Heterocycles* 14(12):1995-1998.
Kirkman, M.A. (Jul. 2009). "Quality of Life in Patients with Leber Hereditary Optic Neuropathy," *Investigative Ophthalmology & Visual Science* 50(7):3112-3115.
Kosmorsky, G. et al. (Feb. 1991). "Neuro-Ophthalmologic Manifestations of Mitochondrial DNA Disorders: Chronic Progressive External Ophthalmoplegia, Kearns-Sayre Syndrome, and Leber's Hereditary Optic Neuropathy," *Neurologic Clinics* 9(1):147-161.
Kovalenko, V.N. et al. (1979). "Vitamin E Activity of Vitamin E Derivatives in Experimental Encephalomalacia in Chicks," *Ukrainskii Biokhimicheskii Zhurnal* 51(6):665-668, Chemical Abstract Only, CAPLUS Abstract No. 1980:74772, 1 page.
Makovetskii, V.P. et al. (1987). "Synthesis, Properties, and Detoxication Activity of α-tocopherol Analogs and Derivatives," *Khimiko-Farmatsevticheskii Zhurnal* 21(12):1441-1446, Chemical Abstract Only, CAPLUS Abstract No. 1988:142850, 2 pages.
Man, P.Y.W. et al. (2002). "Leber Hereditary Optic Neuropathy," *J. Med. Genet.* 39:162-169.
Mayer, H. et al. (1967). "Über die Chemie des Vitamins E. 8. Mitteilung [1]. Die Stereochemie von Natürlichem γ-Tocotrienol (Plastochromanol-3), Plastochromanol-8 und Plastochromanol-8[1])," *Helvetica Chimica Acta* 50(5):1376-1393, No. 139. (English Summary on pp. 1392-1393 and Chemical Abstract CAPLUS Abstract No. 1967:473698 is also included.).
Nishigaki, Y. et al. (2003). "A Novel Mitochondrial tRNA$^{Leu(UUR)}$ Mutation in a Patient with Features of MERRF and Kearns-Sayre Syndrome," *Neuromuscular Disorders* 13:334-340.
Olichon, A. et al. (2006, e-pub. Apr. 20, 2006). "Mitochondrial Dynamics and Disease, OPA1," *Biochimica et Biophysica Acta* 1763:500-509.
Orbis. (2003). "Chronic Progressive External Opthalmoplegia," located at http://telemedicine.orbis.org/bins/volume_page.asp?cid=1-2896-5258-5381&print=true, last visited on Jun. 10, 2014, 1 page.
Packer, L. et al. (Feb. 2001). "Symposium: Molecular Mechanisms of Protective Effects of Vitamin E in Atherosclerosis. Molecular Aspects of α-Tocotrienol Antioxidant Action and Cell Signalling," *The Journal of Nutrition* 131(2):369S-373S.
Pearce, B.C. et al. (1992). "Hypocholesterolemic Activity of Synthetic and Natural Tocotrienols," *Journal of Medicinal Chemistry* 35(20):3595-3606.
Pearce, B.C. et al. (1994). "Inhibitors of Cholesterol Biosynthesis. 2. Hypocholesterolemic and Antioxidant Activities of Benzopyran and Tetrahydronaphthalene Analogues of the Tocotrienols," *Journal of Medicinal Chemistry* 37(4):526-541.
Pelak, V.S. et al. (Sep. 2004). "Neuro-Ophthalmic Manifestations of Neurodegenerative Disease," *Ophthalmology Clinics of North America* 17(3):311-320.
Raghava, S. et al. (2004). "Periocular Routes for Retinal Drug Delivery," *Expert Opin. Drug Deliv.* 1(1):99-114.
Richards, R.M.E. (2004). "Ophthalmic Products," Chapter 26 in *Pharmaceutical Practice*, Third Edition, Winfield, A.J.et al. eds., Churchhill Livingstone, pp. 264-279.
Russo, R. et al. (2008). "Rational Basis for the Development of Coenzyme Q10 as a Neurotherapeutic Agent for Retinal Protection," *Progress in Brain Research* 173:575-582.
Schudel, P. et al. (1963). Über die Chemie des Vitamins E. 5. Mitteilung. Die Synthese von rac. all-trans-ζ$_1$—und-68 -Tocopherol, *Helvetica Chimica Acta* 46(7):2517-2526. (English summary on p. 2526.).

Scott, J.W. et al. (1976). "Syntheses of (2$R$,4'$R$,8'$R$)-α-Tocopherol and (2$R$,3'$E$,7'$E$)-α-Tocotrienol," *Helvetica Chimica Acta* 59:290-306, Nr. 34.
Tabrizi. S.J. et al. (Jul. 1998). "Primary and Secondary Deficiencies of the Mitochondrial Respiratory Chain," *The Neurologist* 4(4):169-179.
Tanito, M. et al. (May 2004). "Distribution of Tocopherols and Tocotrienols to Rat Ocular Tissues After Topical Ophthalmic Administration," *Lipids* 39(5):469-474.
Urano, S. et al. (1983). "Synthesis of $dl$-α-Tocopherol and $dl$-α-Tocotrienol," *Chem. Pharm. Bull.* 31(12):4341-4345.
Wakakura, M. et al. (2009). "Initial Temporal Field Defect in Leber Hereditary Optic Neuropathy," *Jpn. J. Ophthalmol.* 53:603-607.
Yen, M-Y. et al. (2006). "Leber's Hereditary Optic Neuropathy: A Multifactorial Disease," *Progress in Retinal and Eye Research* 25:381-396.
Yu-Wai-Man, P. et al. (2009, e-pub. Nov. 17, 2008). "Inherited Mitochondrial Optic Neuropathies", *J. Med. Genet.* 46:145-158.
Zanna, C. et al. (2008). "OPA1 Mutations Associated with Dominant Optic Atrophy Impair Oxidative Phosphorylation and Mitochondrial Fusion," *Brain* 131(2):352-367.
International Preliminary Report on Patentability mailed on Nov. 1, 2011, for PCT Patent Application No. PCT/US2010/032621, filed on Apr. 27, 2010, six pages.
International Search Report mailed on Jul. 19, 2010, for PCT Patent Application No. PCT/US2010/032621, filed on Apr. 27, 2010, four pages.
Written Opinion mailed on Jul. 19, 2010, for PCT Patent Application No. PCT/US2010/032621, filed on Apr. 27, 2010, five pages.
International Preliminary Report on Patentability mailed on Nov. 1, 2011, for PCT Patent Application No. PCT/US2010/032624, filed on Apr. 27, 2010, seven pages.
International Search Report mailed on Jul. 8, 2010, for PCT Patent Application No. PCT/US2010/032624, filed on Apr. 27, 2010, four pages.
Written Opinion mailed on Jul. 8, 2010, for PCT Patent Application No. PCT/US2010/032624, filed on Apr. 27, 2010, six pages.
International Preliminary Report on Patentability mailed on Oct. 30, 2012 for PCT Patent Application No. PCT/US2011/033983 filed on Apr. 26, 2011, six pages.
International Search Report mailed on Jul. 13, 2011, for PCT Patent Application No. PCT/US11/33983, filed on Apr. 26, 2011, two pages.
Written Opinion mailed on Jul. 13, 2011, for PCT Patent Application No. PCT/US11/33983, filed on Apr. 26, 2011, five pages.
Bertalan L. et al. (2000). "Recovery of fatty oil from the Transylvanian black current by means of supercritical and conventional extraction," *Olaj, szappn Kozmetika* 49(Kulonszam):40-45.
Delettre, C. et al. (2001). "OPA1 (Kjer Type) Dominant Optic Atrophy: A Novel Mitochondrial Disease", *Molecular Genetics and Metabolism*, 75:97-107.
Kanno S. (2006). "Disc Excavation in Hereditary Optic Neuropathies", *Journal of the Eye*, 23(5):587-59.
Milone M. et al. (2009). Mitochondrial disorder with OPA1 mutation lacking optic atrophy, *Mitochondrion*, 9:279-281.
Willard et al. (2001). "Identification of a fatty acid Δ$^6$-desaturase deficiency in human skin fibroblasts", *The Journal of Lipid Research*, 42:501-508.
Olichon, A. et al. Effects of OPA1 Mutations on Mitochondrial Morphology and Apoptosis: Relevance of ADOA Pathogenesis, Journal of Cellular Physiology, Oct. 19, 2006, vol. 211, pp. 423-430.
Yarosh, Will, et al., "The Molecular Mechanisms of OPA1-Mediated Optic Atrophy in Drosophila Model and Prospects for Antioxidant Treatment," PLoS Genet, vol. 4, No. 1, E. 6, Jan. 2008, pp. 62-71.
Wray, S. et al. "Adrenoleukodystrophy with disease of the eye and optic nerve," Am. J, Ophthalmol. 1976 vol. 82, No. 3, pp. 480-5, Abstract only, 1 pp.

\* cited by examiner

Patient (B): OCT

TREATMENT OF LEBER'S HEREDITARY OPTIC NEUROPATHY AND DOMINANT OPTIC ATROPHY WITH TOCOTRIENOL QUINONES

CROSS-REFERENCE TO RELATED APPLICATIONS

This application is a continuation of U.S. patent application Ser. No. 12/768,565, filed Apr. 27, 2010 which claims priority benefit of U.S. Provisional Patent Application Nos. 61/214,795, filed Apr. 28, 2009, and 61/318,733, filed Mar. 29, 2010. The entire contents of those applications are hereby incorporated by reference herein.

TECHNICAL FIELD OF THE INVENTION

The present invention relates to a method of treating Leber's Hereditary Optic Neuropathy (LHON) and dominant optic atrophy (DOA) with tocotrienol quinones (including tocotrienol hydroquinones), for example, alpha-tocotrienol quinone.

BACKGROUND OF THE INVENTION

Leber's Hereditary Optic Neuropathy (LHON) and dominant optic atrophy (DOA) are the most common monosymptomatic inherited optic neuropathies that generally lead to optic nerve degeneration and visual failure.

LHON is a mitochondrial genetic disease characterized by bilateral loss of central vision owing to focal degeneration of the optic nerve. It was first described by Dr. Theodor Leber who reported the characteristic pattern of visual loss in 1871. It was not until 1972 that Dr. Robert Erickson proposed the non-Mendelian pattern of inheritance and suggested a mitochondrial DNA (mtDNA) mutation. The first association with the particular mutation m.11778G>A was not identified until 1988 by Dr. Douglas Wallace. It is now known that over 95% of LHON pedigrees harbor one of three mitochondrial DNA (mtDNA) point mutations m.3460G>A, m.11778G>A and m.14484T>C which all involve genes encoding complex I of the mitochondrial respiratory chain.

The onset of visual loss ranges from age 8 to 60 but occurs mostly between the age of 15 and 30 years. However, visual deterioration can already occur during the first seven years of life. The disease predominantly affects males.

Generally, LHON carriers remain asymptomatic until they experience blurring or clouding of vision in one eye, the second eye becoming affected sequentially with a delay of about six to eight weeks. LHON patients experience a rapid and painless loss of central vision accompanied by the fading of colors especially in the green/red field. Visual acuity usually reaches levels of 20/400 in a few months. At fundus examination the characteristic signs include vascular tortuosity of the central retinal vessels, circumpapillary telangiectatic microangiopathy, swelling of the retinal nerve fiber layer around the disc and lack of leakage on fluorescein angiography. After 6 months optic atrophy is a universal feature. Although visual recovery has been observed in rare cases, the chances of improvement are the least in patients with a point mutation m.11778G>A. LHON is a devastating disorder with the majority of the patients showing no functional improvement and becoming legally blind.

Dominant Optic Atrophy (DOA) also known as autosomal dominant optic atrophy, Kjer type; Kjer optic atrophy; or Kjer's autosomal dominant optic atrophy, is characterized by a slow progressive bilateral loss of central vision starting in childhood and progressing in adult life. It was first described in 1886 by D. Batten. It is an autosomally inherited disease that affects the optic nerves, causing reduced visual acuity and blindness beginning in childhood. This condition is due to mitochondrial dysfunction mediating the death of optic nerve fibers.

Although the visual prognosis is better than compared to LHON, DOA results in significant visual impairment with about half of all affected individuals failing the driving standards, and 13-46% being registered as legally blind. The predominant color defect in DOA is dyschromatopsia involving both the blue-yellow and the red-green axes. Patients with DOA experience diffuse atrophy of the retinal ganglion cell layer, loss of myelin and fibrillary gliosis along the anterior visual pathways extending to the lateral geniculate body.

Vision loss in DOA is due to optic nerve fiber loss from mitochondrial dysfunction. Dominant optic atrophy is associated with mutation of the OPA1 gene. Six other chromosomal genes are described as causing optic atrophy: OPA2 (obscure), OPA3 (dominant), OPA4 (dominant), OPA5 (dominant), OPA6 (recessive) and OPA7 (dominant). Dominant optic atrophy demonstrates genetic heterogeneity, which is where a single disease can be caused by various genetic defects at different loci. Over 60 different mutations of the OPA1 gene causing DOA have been reported.

There is thus a critical and unmet need for effective treatments for Leber's hereditary optic neuropathy and dominant optic atrophy.

SUMMARY OF THE INVENTION

In one embodiment, the invention provides methods of treating Leber's hereditary optic neuropathy and dominant optic atrophy with specific compounds.

In another embodiment, the invention provides methods of treating an individual suffering from Leber's hereditary optic neuropathy or dominant optic atrophy with tocotrienol quinones, comprising administering a therapeutically effective amount of one or more tocotrienol quinones to an individual suffering from Leber's hereditary optic neuropathy or dominant optic atrophy. In another embodiment, the invention provides methods of treating an individual suffering from Leber's hereditary optic neuropathy with alpha-tocotrienol quinone, comprising administering a therapeutically effective amount of alpha-tocotrienol quinone to an individual suffering from Leber's hereditary optic neuropathy. In another embodiment, the invention provides methods of treating an individual suffering from dominant optic atrophy with alpha-tocotrienol quinone, comprising administering a therapeutically effective amount of alpha-tocotrienol quinone to an individual suffering from dominant optic atrophy. In another embodiment, the invention provides methods of treating an individual suffering from Leber's hereditary optic neuropathy with beta-tocotrienol quinone, comprising administering a therapeutically effective amount of beta-tocotrienol quinone to an individual suffering from Leber's hereditary optic neuropathy. In another embodiment, the invention provides methods of treating an individual suffering from dominant optic atrophy with beta-tocotrienol quinone, comprising administering a therapeutically effective amount of beta-tocotrienol quinone to an individual suffering from dominant optic atrophy. In another embodiment, the invention provides methods of treating an individual suffering from Leber's hereditary optic neuropathy with gamma-tocotrienol quinone, comprising administering a therapeutically effective amount of gamma-tocotrienol quinone to an individual suffering from Leber's hereditary optic neuropathy. In another embodiment, the invention provides methods of treating an individual suffering from dominant optic atrophy with gamma-tocotrienol quinone, comprising administering a therapeutically effective amount of gamma-tocotrienol quinone to an individual suffering from dominant optic atrophy. In another embodiment, the invention provides methods of treating an individual suffering from Leber's hereditary optic neuropathy with delta-tocotrienol quinone, comprising administering a therapeutically effective amount of delta-tocotrienol quinone to an individual suffering from Leber's hereditary optic neuropathy. In another embodiment, the invention provides methods of treating an individual suffering from dominant optic atrophy with delta-tocotrienol quinone, comprising administering a therapeutically effective amount of delta-tocotrienol quinone to an individual suffering from dominant optic atrophy.

In another embodiment, the invention provides methods of treating an individual suffering from Leber's hereditary optic neuropathy or dominant optic atrophy with tocotrienol hydroquinones, comprising administering a therapeutically effective amount of one or more tocotrienol hydroquinones to an individual suffering from Leber's hereditary optic neuropathy or dominant optic atrophy. In another embodiment, the invention provides methods of treating an individual suffering from Leber's hereditary optic neuropathy with alpha-tocotrienol hydroquinone, comprising administering a therapeutically effective amount of alpha-tocotrienol hydroquinone to an individual suffering from Leber's hereditary optic neuropathy. In another embodiment, the invention provides methods of treating an individual suffering from dominant optic atrophy with alpha-tocotrienol hydroquinone, comprising administering a therapeutically effective amount of alpha-tocotrienol hydroquinone to an individual suffering from dominant optic atrophy. In another embodiment, the invention provides methods of treating an individual suffering from Leber's hereditary optic neuropathy with beta-tocotrienol hydroquinone, comprising administering a therapeutically effective amount of beta-tocotrienol hydroquinone to an individual suffering from Leber's hereditary optic neuropathy. In another embodiment, the invention provides methods of treating an individual suffering from dominant optic atrophy with beta-tocotrienol hydroquinone, comprising administering a therapeutically effective amount of beta-tocotrienol hydroquinone to an individual suffering from dominant optic atrophy. In another embodiment, the invention provides methods of treating an individual suffering from Leber's hereditary optic neuropathy with gamma-tocotrienol hydroquinone, comprising administering a therapeutically effective amount of gamma-tocotrienol hydroquinone to an individual suffering from Leber's hereditary optic neuropathy. In another embodiment, the invention provides methods of treating an individual suffering from dominant optic atrophy with gamma-tocotrienol hydroquinone, comprising administering a therapeutically effective amount of gamma-tocotrienol hydroquinone to an individual suffering from dominant optic atrophy. In another embodiment, the invention provides methods of treating an individual suffering from Leber's hereditary optic neuropathy with delta-tocotrienol hydroquinone, comprising administering a therapeutically effective amount of delta-tocotrienol hydroquinone to an individual suffering from Leber's hereditary optic neuropathy. In another embodiment, the invention provides methods of treating an individual suffering from dominant optic atrophy with delta-tocotrienol hydroquinone, comprising administering a therapeutically effective amount of delta-tocotrienol hydroquinone to an individual suffering from dominant optic atrophy.

In one embodiment, the pharmaceutical composition used in treating the individual comprises alpha-tocotrienol quinone, where the alpha-tocotrienol quinone comprises at least about 30% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 40% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 50% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 60% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 70% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 75% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 80% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 90% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 95% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 98% by weight of the tocotrienols and tocotrienol quinones present in the preparation. In another embodiment, the pharmaceutical composition used in treating the individual comprises alpha-tocotrienol quinone, where the alpha-tocotrienol quinone comprises at least about 99% by weight of the tocotrienols and tocotrienol quinones present in the preparation.

In one embodiment, the pharmaceutical composition used in treating the individual comprises alpha-tocotrienol quinone, where the alpha-tocotrienol quinone comprises at least about 30% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 40% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 50% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 60% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 70% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 75% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 80% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 90% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 95% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 98% by weight of the material present in the preparation, excluding the weight of any added pharmaceutical carriers or excipients. In another embodiment, the pharmaceutical composition used in treating the individual comprises alpha-tocotrienol quinone, where the alpha-tocotrienol quinone comprises at least about 99% by weight of the material present in the preparation, excluding the weight of any added pharmaceutical carriers or excipients.

In another embodiment, the pharmaceutical preparation contains sufficient alpha-tocotrienol quinone to provide a therapeutic level of compound in at least the retina or the optic nerve system when administered to a patient suffering from LHON or DOA.

In one embodiment, the invention provides unit dosage formulations of between about 50 mg to 500 mg of alpha-tocotrienol quinone, where the purity of the alpha-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% by weight of the tocotrienols and tocotrienol quinones present in the preparation. The unit dosage formulations can be used for treatment of individuals suffering from Leber's hereditary optic neuropathy or dominant optic atrophy.

In one embodiment, the invention provides unit dosage formulations of between about 50 mg to 500 mg of alpha-tocotrienol quinone, where the purity of the alpha-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% of the material present in the preparation, excluding the weight of any added pharmaceutical carriers or excipients. The unit dosage formulations can be used for treatment of individuals suffering from Leber's hereditary optic neuropathy or dominant optic atrophy.

Any of the embodiments of the pharmaceutical compositions, pharmaceutical formulations and unit dosage formulations of alpha-tocotrienol quinone can be used to treat an individual suffering from Leber's hereditary optic neuropathy, such as an individual with Leber's hereditary optic neuropathy where the individual has a 11778G>A point mutation, where the individual has a 3460 G>A point mutation or where the individual has a 14484T>C point mutation.

Any of the embodiments of the pharmaceutical compositions, pharmaceutical formulations and unit dosage formulations of alpha-tocotrienol quinone can be used to treat an individual suffering from dominant optic atrophy, such as an individual with dominant optic atrophy where the individual has mutations in at least one of the OPA genes OPA1, OPA2, OPA3, OPA4, OPA5, OPA6 or OPA7; particularly where the individual has a mutation in the OPA1 gene.

In one embodiment, the pharmaceutical composition used in treating the individual comprises beta-tocotrienol quinone, where the beta-tocotrienol quinone comprises at least about 30% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 40% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 50% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 60% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 70% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 75% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 80% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 90% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 95% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 98% by weight of the tocotrienols and tocotrienol quinones present in the preparation. In another embodiment, the pharmaceutical composition used in treating the individual comprises beta-tocotrienol quinone, where the beta-tocotrienol quinone comprises at least about 99% by weight of the tocotrienols and tocotrienol quinones present in the preparation.

In one embodiment, the pharmaceutical composition used in treating the individual comprises beta-tocotrienol quinone, where the beta-tocotrienol quinone comprises at least about 30% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 40% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 50% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 60% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 70% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 75% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 80% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 90% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 95% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 98% by weight of the material present in the preparation, excluding the weight of any added pharmaceutical carriers or excipients. In another embodiment, the pharmaceutical composition used in treating the individual comprises beta-tocotrienol quinone, where the beta-tocotrienol quinone comprises at least about 99% by weight of the material present in the preparation, excluding the weight of any added pharmaceutical carriers or excipients.

In one embodiment, the invention provides unit dosage formulations of between about 50 mg to 500 mg of beta-tocotrienol quinone, where the purity of the beta-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% by weight of the tocotrienols and tocotrienol quinones present in the preparation. The unit dosage formulations can be used for treatment of individuals suffering from Leber's hereditary optic neuropathy or dominant optic atrophy.

In one embodiment, the invention provides unit dosage formulations of between about 50 mg to 500 mg of beta-tocotrienol quinone, where the purity of the beta-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% of the material present in the preparation, excluding the weight of any added pharmaceutical carriers or excipients. The unit dosage formulations can be used for treatment of individuals suffering from Leber's hereditary optic neuropathy or dominant optic atrophy.

Any of the embodiments of the pharmaceutical compositions, pharmaceutical formulations and unit dosage formulations of alpha-tocotrienol quinone can be used to treat an individual suffering from Leber's hereditary optic neuropathy, such as an individual with Leber's hereditary optic neuropathy where the individual has a 11778G>A point mutation, where the individual has a 3460 G>A mutation or where the individual has a 14484T>C mutation.

Any of the embodiments of the pharmaceutical compositions, pharmaceutical formulations and unit dosage formulations of alpha-tocotrienol quinone can be used to treat an individual suffering from dominant optic atrophy, such as an individual with dominant optic atrophy where the individual has mutations in at least one of the OPA genes OPA1, OPA2, OPA3, OPA4, OPA5, OPA6 or OPA7; particularly where the individual has a mutation in the OPA1 gene.

In one embodiment, the pharmaceutical composition used in treating the individual comprises gamma-tocotrienol quinone, where the gamma-tocotrienol quinone comprises at least about 30% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 40% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 50% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 60% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 70% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 75% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 80% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 90% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 95% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 98% by weight of the tocotrienols and tocotrienol quinones present in the preparation. In another embodiment, the pharmaceutical composition used in treating the individual comprises gamma-tocotrienol quinone, where the gamma-tocotrienol quinone comprises at least about 99% by weight of the tocotrienols and tocotrienol quinones present in the preparation.

In one embodiment, the pharmaceutical composition used in treating the individual comprises gamma-tocotrienol quinone, where the gamma-tocotrienol quinone comprises at least about 30% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 40% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 50% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 60% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 70% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 75% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 80% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 90% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 95% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 98% by weight of the material present in the preparation, excluding the weight of any added pharmaceutical carriers or excipients. In another embodiment, the pharmaceutical composition used in treating the individual comprises gamma-tocotrienol quinone, where the gamma-tocotrienol quinone comprises at least about 99% by weight of the material present in the preparation, excluding the weight of any added pharmaceutical carriers or excipients.

In one embodiment, the invention provides unit dosage formulations of between about 50 mg to 500 mg of gamma-tocotrienol quinone, where the purity of the gamma-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% by weight of the tocotrienols and tocotrienol quinones present in the preparation. The unit dosage formulations can be used for treatment of individuals suffering from Leber's hereditary optic neuropathy or dominant optic atrophy.

In one embodiment, the invention provides unit dosage formulations of between about 50 mg to 500 mg of gamma-tocotrienol quinone, where the purity of the gamma-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% of the material present in the preparation, excluding the weight of any added pharmaceutical carriers or excipients. The unit dosage formulations can be used for treatment of individuals suffering from Leber's hereditary optic neuropathy or dominant optic atrophy.

Any of the embodiments of the pharmaceutical compositions, pharmaceutical formulations and unit dosage formulations of gamma-tocotrienol quinone can be used to treat an individual suffering from Leber's hereditary optic neuropathy, such as an individual with Leber's hereditary optic neuropathy where the individual has a 11778G>A point mutation, where the individual has a 3460 G>A mutation or where the individual has a 14484T>C mutation.

Any of the embodiments of the pharmaceutical compositions, pharmaceutical formulations and unit dosage formulations of gamma-tocotrienol quinone can be used to treat an individual suffering from dominant optic atrophy, such as an individual with dominant optic atrophy where the individual has mutations in at least one of the OPA genes OPA1, OPA2, OPA3, OPA4, OPA5, OPA6 or OPA7; particularly or where the individual has a mutation in the OPA1 gene.

In one embodiment, the pharmaceutical composition used in treating the individual comprises delta-tocotrienol quinone, where the delta-tocotrienol quinone comprises at least about 30% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 40% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 50% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 60% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 70% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 75% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 80% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 90% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 95% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 98% by weight of the tocotrienols and tocotrienol quinones present in the preparation. In another embodiment, the pharmaceutical composition used in treating the individual comprises delta-tocotrienol quinone, where the delta-tocotrienol quinone comprises at least about 99% by weight of the tocotrienols and tocotrienol quinones present in the preparation.

In one embodiment, the pharmaceutical composition used in treating the individual comprises delta-tocotrienol quinone, where the delta-tocotrienol quinone comprises at least about 30% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 40% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 50% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 60% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 70% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 75% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 80% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 90% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 95% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 98% by weight of the material present in the preparation, excluding the weight of any added pharmaceutical carriers or excipients. In another embodiment, the pharmaceutical composition used in treating the individual comprises delta-tocotrienol quinone, where the delta-tocotrienol quinone comprises at least about 99% by weight of the material present in the preparation, excluding the weight of any added pharmaceutical carriers or excipients.

In one embodiment, the invention provides unit dosage formulations of between about 50 mg to 500 mg of delta-tocotrienol quinone, where the purity of the delta-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% by weight of the tocotrienols and tocotrienol quinones present in the preparation. The unit dosage formulations can be used for treatment of individuals suffering from Leber's hereditary optic neuropathy or dominant optic atrophy.

In one embodiment, the invention provides unit dosage formulations of between about 50 mg to 500 mg of delta-tocotrienol quinone, where the purity of the delta-tocotrienol quinone present in the formulation comprises at least about 30%, at least about 40%, at least about 50%, at least about 60%, at least about 70%, at least about 75%, at least about 80%, at least about 90%, at least about 95%, at least about 98%, or at least about 99% of the material present in the preparation, excluding the weight of any added pharmaceutical carriers or excipients. The unit dosage formulations can be used for treatment of individuals suffering from Leber's hereditary optic neuropathy or dominant optic atrophy.

Any of the embodiments of the pharmaceutical compositions, pharmaceutical formulations and unit dosage formulations of delta-tocotrienol quinone can be used to treat an individual suffering from Leber's hereditary optic neuropathy, such as an individual with Leber's hereditary optic neuropathy where the individual has a 11778G>A point mutation, where the individual has a 3460 G>A point mutation or where the individual has a 14484T>C point mutation.

Any of the embodiments of the pharmaceutical compositions, pharmaceutical formulations and unit dosage formulations of delta-tocotrienol quinone can be used to treat an individual suffering from dominant optic atrophy, such as an individual with dominant optic atrophy where the individual has mutations in at least one of the OPA genes OPA1, OPA2, OPA3, OPA4, OPA5, OPA6 or OPA7; particularly where the individual has a mutation in the OPA1 gene.

In one embodiment, the individual suffering from Leber's hereditary optic neuropathy has a mutation affecting Complex I of the mitochondrial electron transport chain In one embodiment, the individual suffering from LHON or DOA, has one or more symptoms selected from the group consisting of: loss of visual acuity, loss of central vision, impairment of color vision, centrocecal scotomas, temporal pallor of the optic disc, circumpapillary telangiectatic microangiopathy, sparing of pupillary light responses, swelling of the retinal nerve fiber layer around the disc (pseudoedema), or optic atrophy.

In one embodiment, administration of a therapeutically effective amount of one or more of alpha-tocotrienol quinone, alpha-tocotrienol hydroquinone, beta-tocotrienol quinone, beta-tocotrienol hydroquinone, gamma-tocotrienol quinone, gamma-tocotrienol hydroquinone, delta-tocotrienol quinone, or delta-tocotrienol hydroquinone, such as a therapeutically effective amount of alpha-tocotrienol quinone, to an individual suffering from LHON, alleviates one or more symptoms selected from the group consisting of: loss of visual acuity, loss of central vision, impairment of color vision, centrocecal scotomas, temporal pallor of the optic disc, circumpapillary telangiectatic microangiopathy, swelling of the retinal nerve fiber layer around the disc (pseudoedema), or optic atrophy.

In one embodiment, administration of a therapeutically effective amount of one or more of alpha-tocotrienol quinone, alpha-tocotrienol hydroquinone, beta-tocotrienol quinone, beta-tocotrienol hydroquinone, gamma-tocotrienol quinone, gamma-tocotrienol hydroquinone, delta-tocotrienol quinone, or delta-tocotrienol hydroquinone, such as a therapeutically effective amount of alpha-tocotrienol quinone, to an individual suffering from DOA, alleviates one or more symptoms selected from the group consisting of: loss of visual acuity, loss of central vision, impairment of color vision, centrocecal scotomas, temporal pallor of the optic disc, circumpapillary telangiectatic microangiopathy, swelling of the retinal nerve fiber layer around the disc (pseudoedema), or optic atrophy.

In one embodiment, the compound used in treatment is able to stop progression of: loss of visual acuity, loss of central vision, impairment of color vision, centrocecal scotomas, temporal pallor of the optic disc, circumpapillary telangiectatic microangiopathy, swelling of the retinal nerve fiber layer around the disc (pseudoedema), or optic atrophy.

In one embodiment, the compound used in treatment stops progression of visual activity. In another embodiment, the compound used in treatment stops progression of loss of color vision.

In one embodiment, the compound used in treatment improves the visual acuity from below 20/400, or from below about 20/400, to 20/100, to about 20/100, or to better than 20/100. In another embodiment, the compound used in treatment improves color vision.

In one embodiment, the compound used for treatment is administered to the patient in an amount such that the concentration of the compound in the plasma of the patient is between about 1 ng/ml and about 5,000 ng/ml. In one embodiment, the compound used for treatment is administered to the patient in an amount such that the concentration of the compound in the plasma of the patient is between about 10 ng/ml and about 2,000 ng/ml. In one embodiment, the compound used for treatment is administered to the patient in an amount such that the concentration of the compound in the plasma of the patient is between about 10 ng/ml and about 2,000 ng/ml. In one embodiment, the compound used for treatment is administered to the patient in an amount such that the concentration of the compound in the plasma of the patient is between about 10 ng/ml and about 1,000 ng/ml. In one embodiment, the compound used for treatment is administered to the patient in an amount such that the concentration of the compound in the plasma of the patient is between about 10 ng/ml and about 500 ng/ml. In one embodiment, the compound used for treatment is administered to the patient in an amount such that the concentration of the compound in the plasma of the patient is between about 10 ng/ml and about 250 ng/ml. In one embodiment, the compound used for treatment is administered to the patient in an amount such that the concentration of the compound in the plasma of the patient is between about 10 ng/ml and about 150 ng/ml. In one embodiment, the compound used for treatment is administered to the patient in an amount such that the concentration of the compound in the plasma of the patient is between about 10 ng/ml and about 100 ng/ml. In one embodiment, the compound used for treatment is administered to the patient in an amount such that the concentration of the compound in the plasma of the patient is about 50 ng/ml.

In one embodiment, the compound for use in treating LHON or DOA is selected from the group consisting of alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or any combination of two or more of the foregoing compounds, and is formulated in a pharmaceutical preparation suitable for administration via feeding tube, feeding syringe, or gastrostomy. In another embodiment, the compound for use in treating LHON or DOA is selected from the group consisting of alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or any combination of two or more of the foregoing compounds, and is formulated in a pharmaceutical preparation comprising one or more vegetable-derived oils, such as sesame oil, and/or one or more animal-derived oils, and/or one or more fish-derived oils. In another embodiment, the compound for use in treating LHON or DOA is alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or any combination of two or more of the foregoing compounds, and is formulated in a pharmaceutical preparation comprising one or more vegetable-derived oils, such as sesame oil, and/or one or more animal-derived oils, and/or one or more fish-derived oils, where the pharmaceutical preparation is suitable for oral administration.

In some embodiments, the invention relates to a topical, periocular, or intraocular ophthalmic formulation comprising an ophthalmically effective amount of alpha-tocotrienol quinone.

In some embodiments, the ophthalmic formulations of the present invention are administered locally in eye drops. In other embodiments, the ophthalmic formulations of the present invention are administered as an irrigating solution. In other embodiments, the ophthalmic formulations of the present invention are administered periocularly. In other embodiments, the ophthalmic formulations of the present invention are administered intraocularly.

In another aspect, the invention relates to a topical ophthalmic formulation beneficial for in a patient suffering from or at risk of ophthalmic disorders or vision loss from LHON or DOA, said formulation comprising an ophthalmically effective amount of one or more agents selected from the group consisting of alpha-tocotrienol quinone, beta-tocotrienol quinone, gamma-tocotrienol quinone, and delta-tocotrienol quinone, or mixtures thereof; and an ophthalmically acceptable vehicle.

In another embodiment, the invention relates to the topical, periocular, or intraocular use of a formulation comprising alpha-tocotrienol quinone to prevent, reduce, ameliorate or treat LHON or DOA in individuals in need of such treatment. In another embodiment, the invention relates to the topical, periocular, or intraocular use of a formulation comprising beta-tocotrienol quinone to prevent, reduce, ameliorate or treat LHON or DOA in individuals in need of such treatment. In another embodiment, the invention relates to the topical, periocular, or intraocular use of a formulation comprising gamma-tocotrienol quinone to prevent, reduce, ameliorate or treat LHON or DOA in individuals in need of such treatment. In another embodiment, the invention relates to the topical, periocular, or intraocular use of a formulation comprising delta-tocotrienol quinone to prevent, reduce, ameliorate or treat LHON or DOA in individuals in need of such treatment.

In another embodiment, the invention relates to a topical ophthalmic formulation comprising a tocotrienol quinone, beneficial for protection against, reduction of, amelioration of, or treatment of an ophthalmic disorder associated with a disease selected from Leber's Hereditary Optic Neuropathy (LHON) or dominant optic atrophy (DOA).

For all of the compounds and methods described herein which use a tocotrienol quinone, the quinone form can also be used in its reduced (hydroquinone, 1,4-benzenediol) form when desired. Likewise, the hydroquinone form can also be used in its oxidized (quinone) form when desired.

For all of the compounds and methods described herein, the invention also encompasses the use in treatment of the compounds and methods disclosed. The invention also encompasses the use of the compounds described herein for preparation of a medicament for use in treating Leber's hereditary optic neuropathy. The invention also encompasses the use of the compounds described herein for preparation of a medicament for use in treating dominant optic atrophy.

The present invention comprises multiple aspects, features and embodiments, where such multiple aspects, features and embodiments can be combined and permuted in any desired manner. These and other aspects, features and embodiments of the present invention will become evident upon reference to the remainder of this application, including the following detailed description. In addition, various references are set forth herein that describe in more detail certain compositions, and/or methods; all such references are incorporated herein by reference in their entirety.

DETAILED DESCRIPTION OF THE INVENTION

Figure 1:
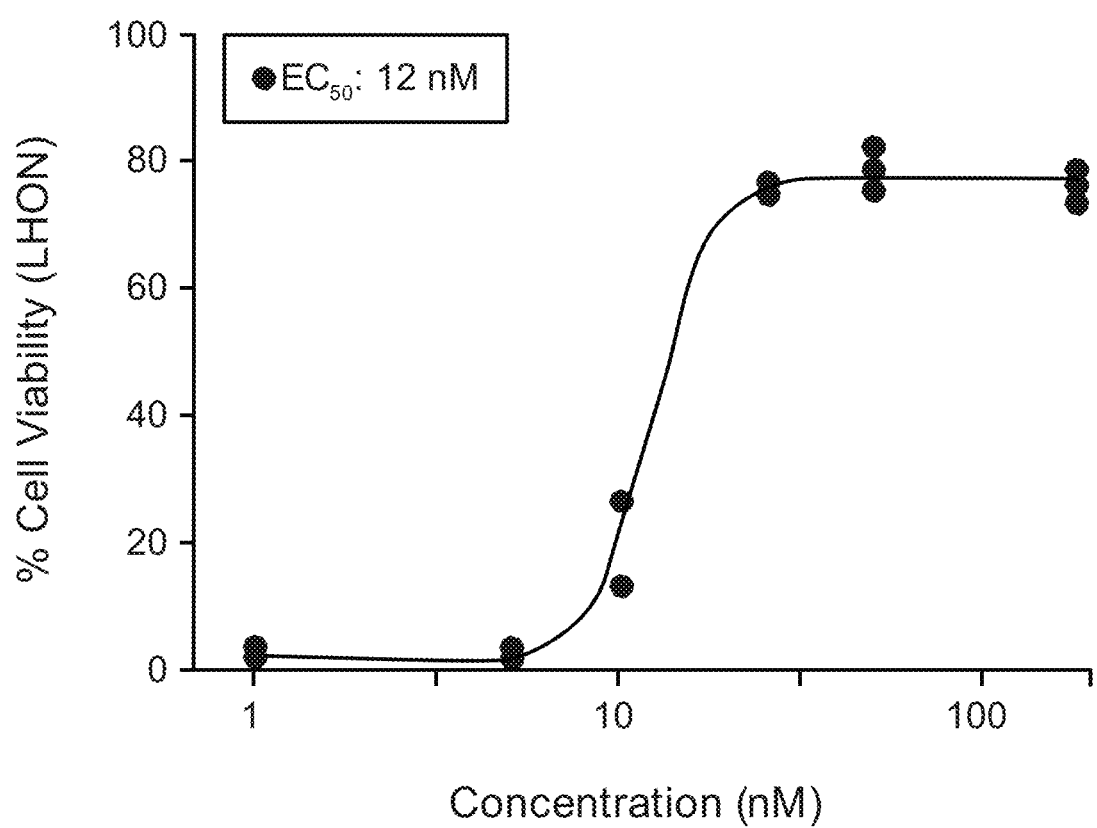
FIG. 1 illustrates a graph showing the viability of cells with a LHON mutation obtained from the Coriell Cell Repositories (Camden, N.J.; repository number GM03858) in the presence of alpha-tocotrienol quinone ($\alpha$TTQ). Alpha-tocotrienol quinone displayed an $EC_{50}$ of 12 nM.
Figure 2:
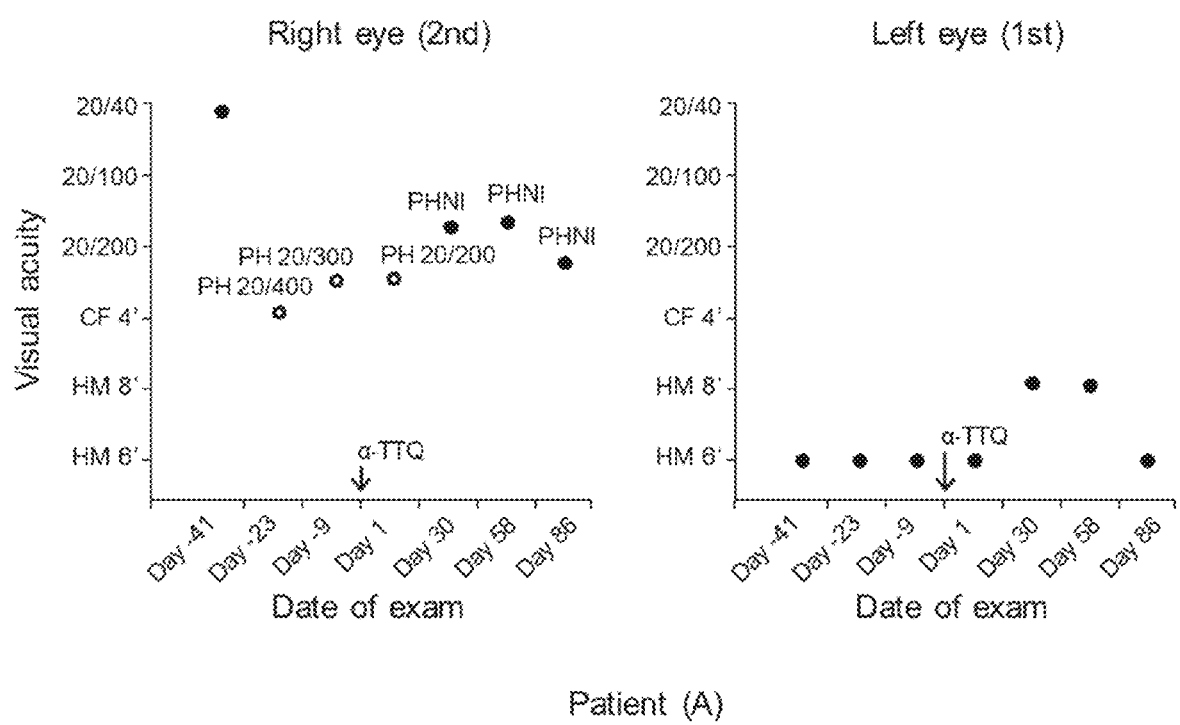
FIG. 2 illustrates two graphs showing the visual acuity of the right eye and the left eye of Patient (A) who has a LHON 11778 mutation, in response to the treatment with alpha-tocotrienol quinone ($\alpha$TTQ). Patient (A) also suffers from retinopathy in her left eye. Treatment with alpha-tocotrienol quinone improved the visual acuity of the right eye from 20/400 to 20/200. The visual acuity of the left eye that has retinopathy was also improved by a slight degree.
Figure 3:
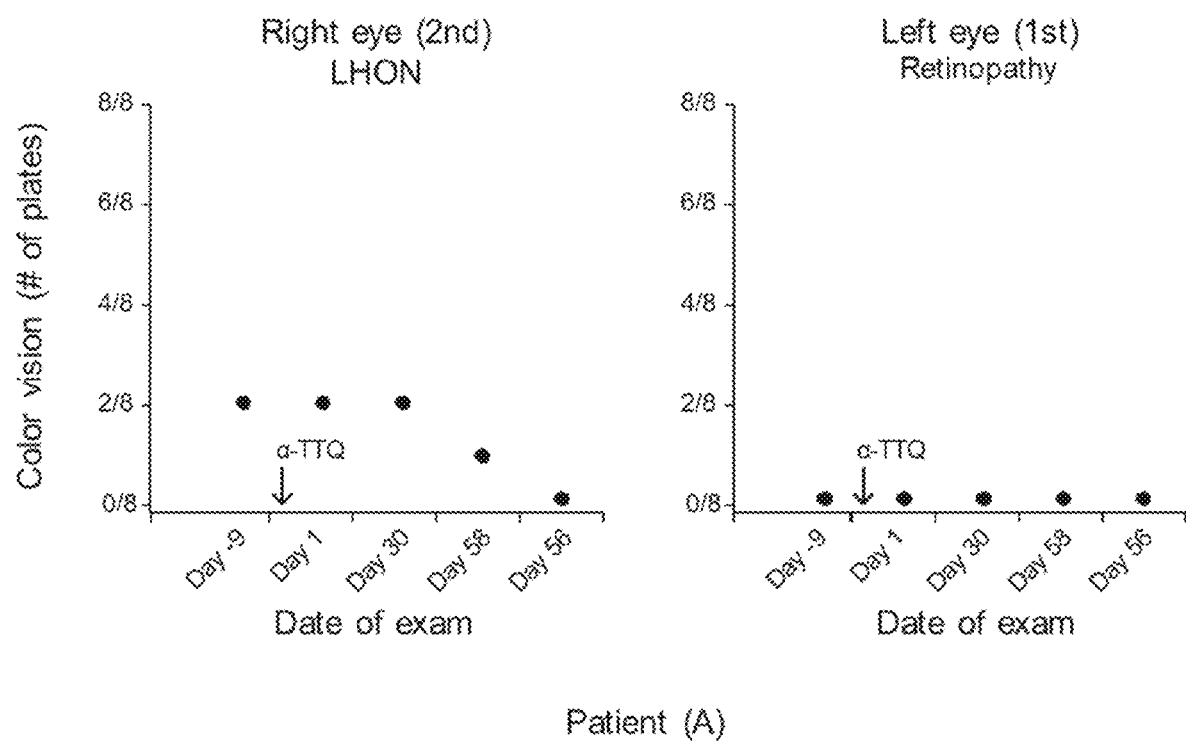
FIG. 3 illustrates two graphs showing the results of the Ishihura Color Vision Test performed with 8 plates. The color vision in both eyes of Patient (A) has not deteriorated from baseline.
Figure 4:
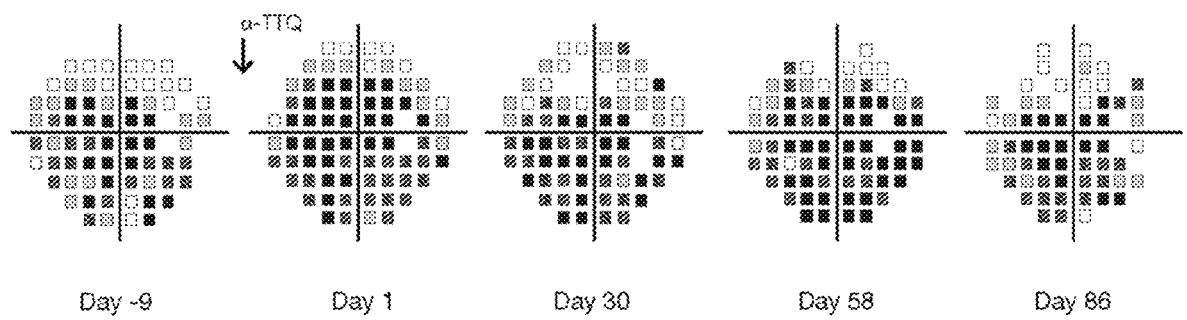
FIG. 4 illustrates the visual field of Patient (A). The left eye suffering from retinopathy cannot be measured. A major improvement in the visual field of the left eye is shown on Day 30 after treatment with alpha-tocotrienol quinone ($\alpha$TTQ).
Figure 5:
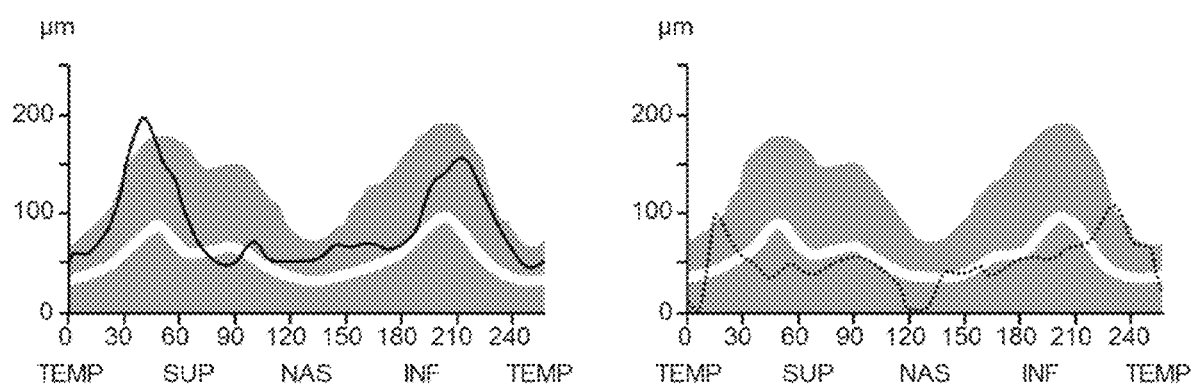
FIG. 5 illustrates the slope of retinal thickness in Patient (A) eyes as measured with optical coherence tomography (OCT) on Day 5 after treatment with alpha-tocotrienol quinone ($\alpha$TTQ).
Figure 6:
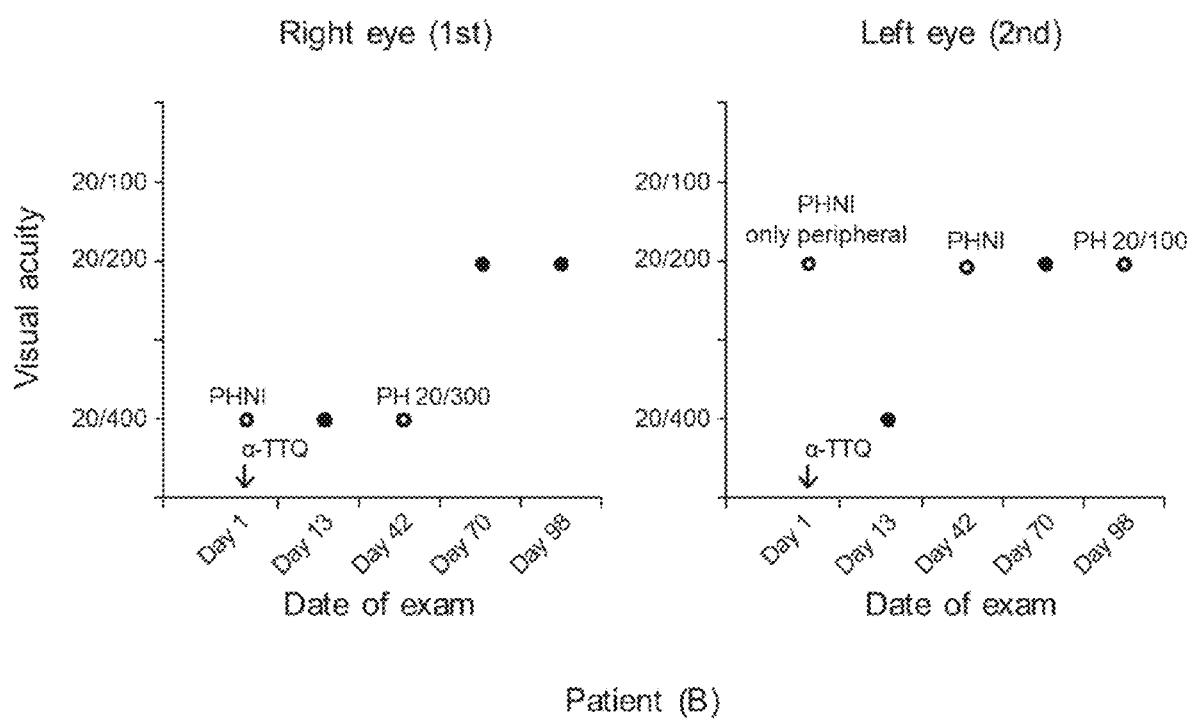
FIG. 6 illustrates two graphs showing the visual acuity of the right eye and the left eye of Patient (B) with a LHON 11778 mutation in response to the treatment with alpha-tocotrienol quinone ($\alpha$TTQ). Improvement is seen in both eyes.
Figure 7:
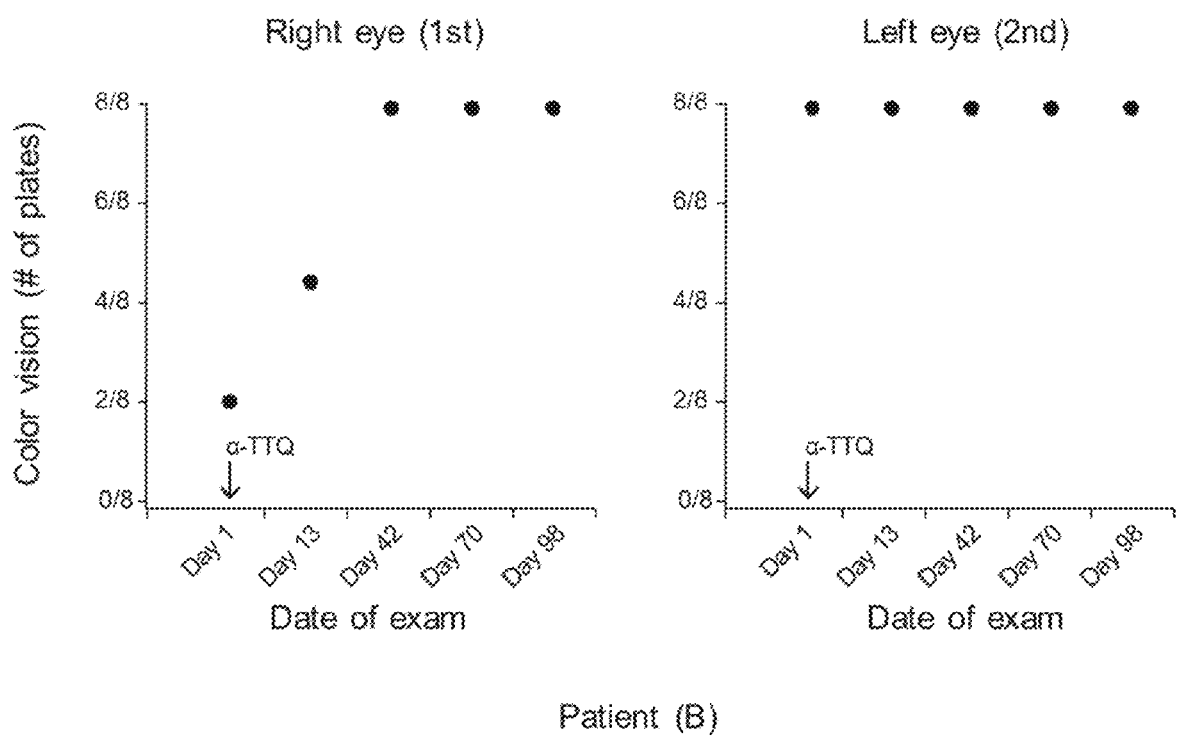
FIG. 7 illustrates two graphs showing the results of the Ishihura Color Vision Test performed with 8 plates. The color vision of the left eye of Patient (B) has improved to normal where his right eye was before treatment.
Figure 8:
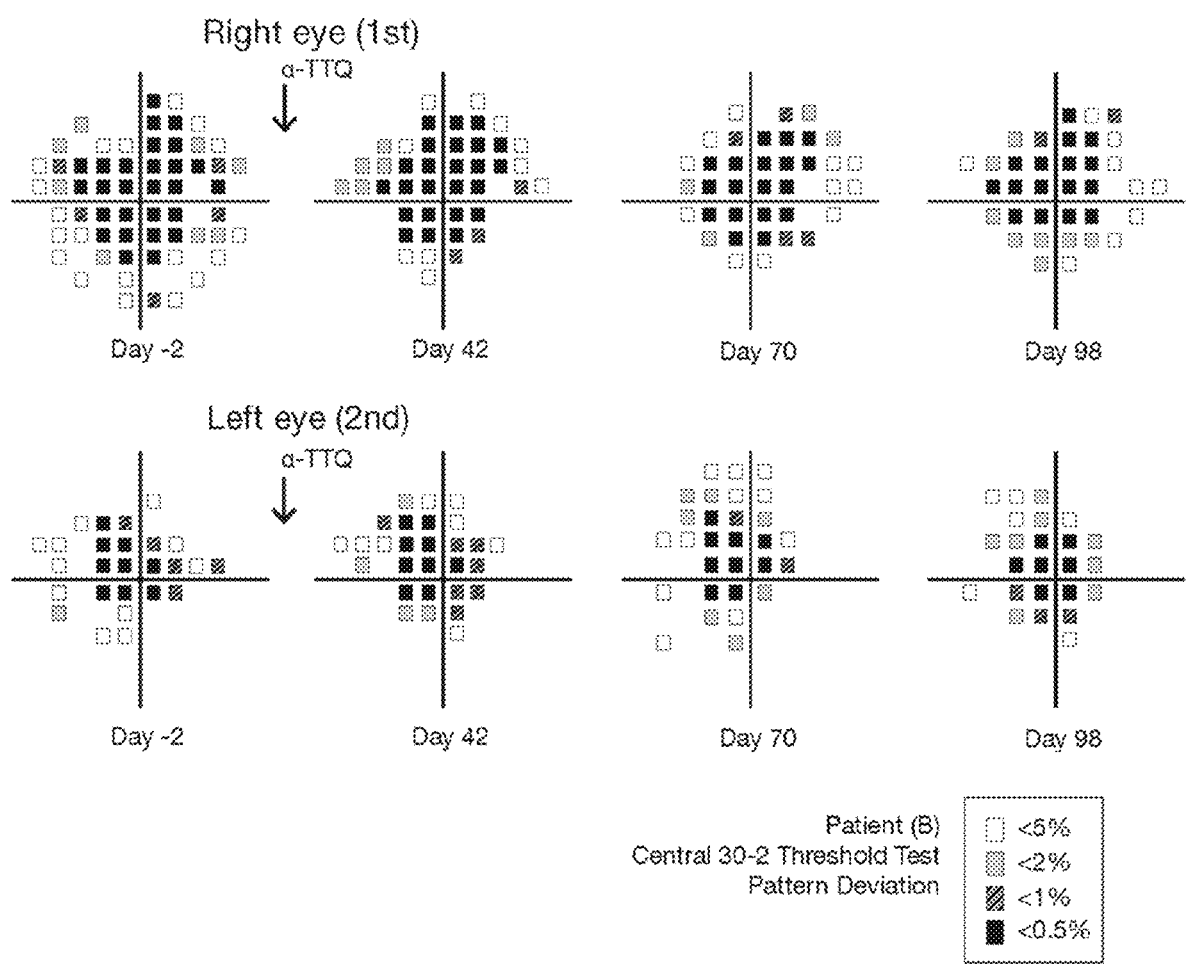
FIG. 8 illustrates the visual field of both eyes from Patient (B). Some improvement in both eyes is shown on Day 41 after treatment with alpha-tocotrienol quinone ($\alpha$TTQ).
Figure 9:
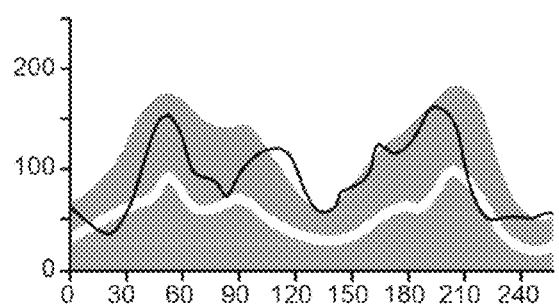
FIG. 9 illustrates the slope of retinal thickness in Patient (B) eyes as measured with optical coherence tomography (OCT) on Day 15 after treatment with alpha-tocotrienol quinone ($\alpha$TTQ).
Figure 9:
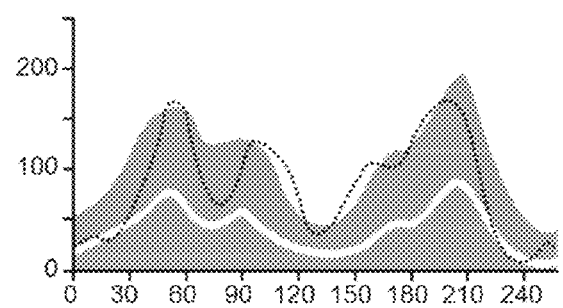

The present invention relates to a method of treating Leber's hereditary optic neuropathy or dominant optic atrophy, with specific compounds.

In one aspect, tocotrienol quinones are contemplated for use in treatment, including alpha-tocotrienol quinone, beta-tocotrienol quinone, gamma-tocotrienol quinone, and delta-tocotrienol quinone. In another aspect, alpha-tocotrienol quinone is contemplated for use in treatment. Structures of tocotrienol quinones are given in Table 1 below. The tocotrienol quinones with the naturally occurring tocotrienol configuration are used in one embodiment of the invention, but other stereoisomers and/or mixtures of stereoisomers in any ratio, such as racemic mixtures, can also be used in the invention.

Tocotrienol quinones can be used in their oxidized form, as shown in Table 1, or can be used in their reduced hydroquinone form, as shown in Table 2. The quinone (cyclohexadienedione) form and hydroquinone (benzenediol) form are readily interconverted with appropriate reagents. The quinone can be treated in a biphasic mixture of an ethereal solvent with a basic aqueous solution of $Na_2S_2O_4$ (Vogel, A. I. et al. Vogel's Textbook of Practical Organic Chemistry, $5^{th}$ Edition, Prentice Hall: New York, 1996; Section 9.6.14 Quinones, "Reduction to the Hydroquinone"). Standard workup in the absence of oxygen yields the desired hydroquinone. The hydroquinone form can be oxidized to the quinone form with oxidizing agents such as ceric ammonium nitrate (CAN) or ferric chloride. The quinone and hydroquinone forms are also readily interconverted electrochemically, as is well known in the art. See, e.g., Section 33.4 of Streitweiser & Heathcock, Introduction to Organic Chemistry, New York: Macmillan, 1976.

TABLE 1

Tocotrienol quinones

| | | R¹ | R² | R³ |
|---|---|---|---|---|
| Alpha-tocotrienol quinone | | methyl | methyl | methyl |
| Beta-tocotrienol quinone | | methyl | H | methyl |
| Gamma-tocotrienol quinone | | H | methyl | methyl |
| Delta-tocotrienol quinone | | H | H | methyl |

TABLE 2

Tocotrienol hydroquinones

| | | R¹ | R² | R³ |
|---|---|---|---|---|
| Alpha-tocotrienol hydroquinone | | methyl | methyl | methyl |

TABLE 2-continued

Tocotrienol hydroquinones

| Compound | Structure | R¹ | R² | R³ |
|---|---|---|---|---|
| | (general structure with R¹, R², R³) | | | |
| Beta-tocotrienol hydroquinone | | methyl | H | methyl |
| Gamma-tocotrienol hydroquinone | | H | methyl | methyl |
| Delta-tocotrienol hydroquinone | | H | H | methyl |

By "individual," "subject," or "patient," is meant a mammal, preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total.

Because LHON and DOA are due to genetic mutations, genetic screening can be used to identify patients at risk of the disease. LHON can arise from mutations in Complex I of the mitochondrial respiratory chain. The compounds disclosed herein can be administered to, and the methods of the invention disclosed herein can be used to treat, asymptomatic patients with mutations in Complex I, who are at risk of developing the clinical symptoms of the disease, in order to suppress the appearance of any adverse symptoms or lessen the severity of symptoms that may occur. The compounds disclosed herein can be administered to, and the methods of the invention disclosed herein can be used to treat, symptomatic patients with mutations in Complex I, particularly including, but not limited to, the point mutations 11778G>A, 3460 G>A, or 14484T>C, in order to treat the disease.

The compounds disclosed herein can be administered to, and the methods of the invention disclosed herein can be used to treat, asymptomatic patients with mutations in OPA genes, such as OPA1, OPA2, OPA3, OPA4, OPA5, OPA6 or OPA7 who are at risk of developing the clinical symptoms of the optic disease, in order to suppress the appearance of any adverse symptoms or lessen the severity of symptoms that may occur. The compounds disclosed herein can be administered to, and the methods of the invention disclosed herein can be used to treat, symptomatic patients with mutations in OPA genes, such as OPA1, OPA2, OPA3, OPA4, OPA5, OPA6 or OPA7. The compounds disclosed herein can be administered to, and the methods of the invention disclosed herein can be used to treat, symptomatic patients with mutations in the OPA1 gene.

"Therapeutic use" of the compounds discussed herein is defined as using one or more of the compounds discussed herein to treat or suppress a disease, as defined above. A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The description of compounds herein also includes all stereoisomers of the compounds, including diastereomers and enantiomers, and mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds disclosed herein and esters of compounds disclosed herein. Further discussion of suitable prodrugs is provided in H. Bundgaard, *Design of Prodrugs*, New York: Elsevier, 1985; in R. Silverman, *The Organic Chemistry of Drug Design and Drug Action*, Boston: Elsevier, 2004; in R. L. Juliano (ed.), *Biological Approaches to the Controlled Delivery of Drugs* (Annals of the New York Academy of Sciences, v. 507), New York: New York Academy of Sciences, 1987; and in E. B. Roche (ed.), *Design of Biopharmaceutical Properties Through Prodrugs and Analogs* (Symposium sponsored by Medicinal Chemistry Section, APhA Academy of Pharmaceutical Sciences, November 1976 national meeting, Orlando, Fla.), Washington: The Academy, 1977.

Monitoring Treatment Efficacy

Routine Plasma Analytes:

Blood ketone body ratios, including lactate: pyruvate and beta-hydroxy butyrate:acetoacetate, reflect electron balance. Alterations in these ratios can be used to assess systemic metabolic function. Increased blood lactate, increased blood pyruvate, increased blood alanine, and blood pH (to check for metabolic acidosis) can also be monitored.

Metabolomic Analysis of Plasma and Urine:

Urine analysis can be performed on the patient, and can include measurement of the following organic acids: lactic acid, pyruvic acid, succinic acid, fumaric acid, 2-ketoglutaric acid, methyl malonic acid, 3-OH butyric acid, acetoacetic acid, 2-keto-3-methylvaleric acid, 2-keto-isocaproic acid, 2-keto-isovaleric acid, ethylmalonic acid, adipic acid, suberic acid, sebacic acid, 4-OH-phenylacetic acid, 4-OH-phenyllactic acid, 4-OH-phenylpyruvic acid, succinylacetone, and creatinine. Urine analysis performed on the patient can also include measurement of the following amino acids: proline, glutamine, threonine, serine, glutamic acid, arginine, glycine, alanine, histidine, lysine, valine, asparagine, methionine, phenylalanine, isoleucine, leucine, tyrosine, hydroxyproline, creatinine, aspartic acid, cysteine, ornithine, citrulline, homocysteine, and taurine. In a panel of metabolic analytes, the following can be measured: sodium, potassium, chloride, bicarbonate, anion gap, glucose (serum), urea nitrogen (blood), creatinine, calcium, bilirubin, aspartate amino transferase, alanine amino transferase, alkaline phosphatase, total protein (serum), albumin (serum), and hemolysis index. Recently, the Critical Path Initiative has put forth a battery of biomarkers to predict drug toxicity that can also reflect renal mitochondrial function. Alterations in KIM-1, Albumin, Total Protein, $\beta$2-microglobulin, Cystatin C, Clusterin, Trefoil Factor-3, and Neutrophil Gelatinase-Associated Lipocalin can be used to both detect (if present) a subclinical nephropathy and assemble a more accurate depiction of renal function. Finally, Haas, et al. Mol Genet Metab. (2008) 94(1): 16-37 describes various tests, such as MRS-based biochemical analysis, that can be used in the present invention.

Optical Coherence Tomography (OCT):

OCT is a non-invasive technology used for imaging the retina, the multi-layered sensory tissue lining the back of the eye. OCT, the first instrument to allow doctors to see cross-sectional images of the retina, is revolutionizing the early detection and treatment of eye conditions such as macular holes, pre-retinal membranes, macular swelling and even optic nerve damage. Retinal thickness may also be measured using other devices such as the Retinal Thickness Analyzer (RTA; Talia Technology, Ltd., Mevasseret Zion, Israel) and the Heidelberg Retina Tomograph (HRT; Heidelberg Engineering GmbH, Heidelberg, Germany). Persons skilled in the art will appreciate that the slope of retinal thickness may be calculated over any number of distances, and that the smallest distance is only limited by the resolution of the devices used to practice the methods of the invention.

Ishihara Color Test:

The Ishihara Color test is a test for red-green color deficiencies. The test consists of a number of colored plates, called Ishihara plates, each of which contain a circle of dots appearing randomized in color and size. Within the pattern are dots which form a number visible to those with normal color vision and invisible, or difficult to see, for those with a red-green color vision defect. The full test consists of 38 plates, but the existence of a deficiency is usually clear after a few plates. Testing the first 24 plates gives a more accurate diagnosis of the severity of the color vision defect.

Common plates include a circle of dots in shades of green and light blues with a figure differentiated in shades of brown, or a circle of dots in shades of red, orange and yellow with a figure in shades of green; the first testing for protanopia and the second for deuteranopia.

Leber's Hereditary Optic Neuropathy and Dominant Optic Atrophy: Symptoms Amenable to Treatment.

LHON gives rise to several devastating symptoms, including loss of visual acuity, loss of central vision, impairment of color vision, centrocecal scotomas, temporal pallor of the optic disc, circumpapillary telangiectatic microangiopathy, swelling of the retinal nerve fiber layer around the disc (pseudoedema), or optic atrophy. Sparing of the pupillary light response is observed in LHON and is useful in differentiating LHON from other optical disorders (see Bremner, F. D., "Pupil assessment in optic nerve disorders," *Eye* (2004) 18, 1175-1181).

Symptoms of DOA are similar to those of LHON. These symptoms include bilateral loss of central vision starting in childhood and variably progressing in adult life, centrocecal scotomas, impairment of colors vision and temporal pallor of the optic disc, optic atrophy and optic disc excavation (see Carelli, V., "Retinal Ganglion Cell Neurodegeneration in Mitochondrial Inherited Disorders," *Biochimica et Biophysica Acta*. 2009; 1787:518-528).

In one embodiment, the methods of the invention can alleviate one or more symptoms of LHON or DOA, including loss of visual acuity, loss of central vision, impairment of color vision, centrocecal scotomas, temporal pallor of the optic disc, circumpapillary telangiectatic microangiopathy, swelling of the retinal nerve fiber layer around the disc (pseudoedema), or optic atrophy. In one embodiment, the methods of the invention can alleviate one or more symptoms of LHON or DOA, including loss of visual acuity, loss of central vision, or impairment of color vision.

Mutations Causing Leber's Hereditary Optic Neuropathy

Several mutations in genes involved in energy metabolism are implicated in LHON. Said mutations affect Complex I in the mitochondrial electron transport chain.

Individuals with mutations in these genes who do not presently manifest symptoms of LHON, can be treated with the methods of the invention in order to suppress symptoms of LHON, or to lessen the severity of symptoms of LHON once they develop. Accordingly, in one aspect, the invention comprises methods of administering specific compounds, such as tocotrienol quinones, to individuals who have one or more of the mutations listed herein. In another aspect, the invention comprises methods of administering alpha-tocotrienol quinone to individuals who have one or more of the mutations listed herein.

LHON disorders arising from mutations that affect Complex I are of interest for the present invention. These mutations include, but are not limited to, point mutation 11778G>A, point mutation 3460 G>A, or point mutation 14484T>C.

Mutations Causing Dominant Optic Atrophy (DOA)

Several mutations in genes involved in energy metabolism are implicated in DOA. Said mutations affect the OPA genes mapped to chromosome 3q28-qter. In 2000 the OPA1 gene was identified by Delettre et al, "Nuclear gene OPA1, encoding a mitochondrial dynamin-related protein, is mutated in dominant optic atrophy", *Nat. Genet*. 2000, 26: 207-210 and Alexander et al. "OPA1 encoding a dynamin-related GTPase, is mutated in autosomal dominant optic atrophy linked to chromosome 3q28", *Nat Genet*. 2000, 26: 211-215. A small number of families with DOA have been mapped to other chromosomal OPA3, OPA4, OPA5, and OPA7 genes (Yu-Wai-Man et al., "Inherited Mitochondrial Optic Neuropathies", *J. Med. Genet*. 2009, 46:145-158.

Individuals with mutations in these genes who do not presently manifest symptoms of DOA, can be treated with the methods of the invention in order to suppress symptoms of DOA, or to lessen the severity of symptoms of DOA once they develop. Accordingly, in one aspect, the invention comprises methods of administering specific compounds, such as tocotrienol quinones, to individuals who have one or more of the mutations listed herein. In another aspect, the invention comprises methods of administering alpha-tocotrienol quinone to individuals who have one or more of the mutations listed herein.

Optic disorders arising from mutations that affect Complex I or OPA genes are of interest for the present invention. These mutations include, but are not limited to, point mutation 11778G>A, point mutation, 3460 G>A, or point mutation 14484T>C in Complex I; or OPA1, OPA2, OPA3, OPA4, OPA5, OPA6 or OPA7, particularly OPA1.

Dosages

The compounds used in the methods of the invention can be administered in various amounts. Examples of daily dosages which can be used are an effective amount within the dosage range of about 0.1 mg/kg to about 300 mg/kg body weight, or within about 0.1 mg/kg to about 100 mg/kg body weight, or within about 0.1 mg/kg to about 80 mg/kg body weight, or within about 0.1 mg/kg to about 50 mg/kg body weight, or within about 0.1 mg/kg to about 30 mg/kg body weight, or within about 0.1 mg/kg to about 10 mg/kg body weight, or within about 1.0 mg/kg to about 80 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 80 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight, or about or up to about 1, about or up to about 5, about or up to about 10, about or up to about 15, about or up to about 20, about or up to about 25, about or up to about 30, about or up to about 40, about or up to about 50, about or up to about 60, about or up to about 70, about or up to about 75, about or up to about 80, about or up to about 90, about or up to about 100, about or up to about 125, about or up to about 150, about or up to about 175, about or up to about 200, about or up to about 225, about or up to about 250, about or up to about 275, about or up to about 300, about or up to about 325, about or up to about 350, about or up to about 375, about or up to about 400, about or up to about 425, about or up to about 450, about or up to about 500, about or up to about 550, about or up to about 600, about or up to about 650, about or up to about 700, about or up to about 750, about or up to about 800, about or up to about 850, about or up to about 900, about or up to about 950, or about or up to about 1000 mg total. The compound(s) may be administered in a single daily dose, or the total daily dosage may be administered in divided dosage of two, three or four times daily. These dosages can be administered long term, for example, over months, years, or even over the entire lifetime of the patient.

The particular dosage appropriate for a specific patient is determined by dose titration. For example, animal studies of alpha-tocotrienol quinone administration have shown that in rats, at 10 mg/kg, bioavailability is high (~90%), $C_{max}$=931 ng/mL, $T_{max}$=3.5 h and $t_{1/2}$=3.5 h. There is less than dose-proportionality since for an increase in doses of 2.4:6:10:20 there is only an increase in AUCs of 1.5:2.8:4.0:6.7. This lack of dose-proportionality may be due to decreased absorption since there is no change in $t_{1/2}$ over dose range. Alpha-tocotrienol quinone tested in rats was safe when given acutely up to 2000 mg/kg. In fasted dogs, at 10 mg/kg, bioavailability is low (~16%), $C_{max}$=442 ng/mL, $T_{max}$=2.8 h and $t_{1/2}$=7.6 h.

The single dose and repeat dose plasma profiles for alpha tocotrienol quinone were simulated using a dose adjusted to achieve a $C_{max}$<10 µM and a $C_{min}$>0.5 µM. Assuming a daily dose and linear kinetics, for a 70 kg adult the total dose would need to be 379 mg (5.41 mg/kg) to achieve a $C_{24h}$ of 220.5 ng/ml (0.5 µM).

The starting dose can be estimated based on the United States Food and Drug Administration guidelines titled "Estimating the Maximum Safe Starting Dose in Initial Clinical Trials for Therapeutics in Adult Healthy Volunteers" (July 2005) as well as the International Conference on Harmonisation of Technical Requirements for Registration of Pharmaceuticals for Human Use (ICH) guidelines titled "Guidance on Non-clinical Safety Studies for the Conduct of Human Clinical Trials and Marketing Authorization for Pharmaceuticals" (July 2008). Per ICH guidelines, predicted exposures from the starting dose should not exceed $\frac{1}{50}^{th}$ the NOAEL (No-Adverse-Observed-Effect-Level) in the more sensitive species on a mg/m$^2$ basis. Following a single oral dose of alpha-tocotrienol quinone, the NOAEL was established to be 500 mg/kg for the female rat, i.e. 3,000 mg/m2. This dosage would be equivalent to 81 mg/kg in an adult human. $\frac{1}{50}$th of 81 mg/kg is 1.6 mg/kg, i.e. 110 mg for a 70 kg adult, or 16 mg for a 10 kg child. This dose can be administered once, twice, or three times daily.

Co-Administered Agents

While the compounds described herein can be administered as the sole active pharmaceutical agent, they can also be used in combination with one or more other agents used in the treatment or suppression of LHON or DOA. Representative agents useful in combination with the compounds described herein for the treatment or suppression of LHON or DOA include, but are not limited to, Coenzyme Q, including Coenzyme Q10; idebenone; MitoQ; acetylcarnitine (such as acetyl-L-carnitine or acetyl-DL-carnitine); palmitoylcarnitine (such as palmitoyl-L-carnitine or palmitoyl-DL-carnitine); carnitine (such as L-carnitine or DL-carnitine); quercetine; mangosteen; acai; uridine; N-acetyl cysteine (NAC); polyphenols, such as resveratrol; Vitamin A; Vitamin C; lutein; beta-carotene; lycopene; glutathione; fatty acids, including omega-3 fatty acids such as α-linolenic acid (ALA), eicosapentaenoic acid (EPA), and docosahexaenoic acid (DHA); lipoic acid and lipoic acid derivatives; Vitamin B complex; Vitamin B1 (thiamine); Vitamin B2 (riboflavin); Vitamin B3 (niacin, nicotinamide, or niacinamide); Vitamin B5 (pantothenic acid); Vitamin B6 (pyridoxine or pyridoxamine); Vitamin B7 (biotin); Vitamin B9 (folic acid, also known as Vitamin B11 or Vitamin M); Vitamin B12 (cobalamins, such as cyanocobalamin); inositol; 4-aminobenzoic acid; folinic acid; Vitamin E; other vitamins; and antioxidant compounds.

The co-administered agents can be administered simultaneously with, prior to, or after, administration of the primary compound intended to treat LHON or DOA.

Formulations and Routes of Administration

The compounds used in the methods of the invention may be administered in any suitable form that will provide sufficient plasma levels of the compounds. The compounds can be administered enterally, orally, parenterally, sublingually, by inhalation (e.g. as mists or sprays), rectally, or topically in unit dosage formulations containing conventional nontoxic pharmaceutically acceptable carriers, excipients, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. The term parenteral as used herein includes subcutaneous injections, intravenous injection, intraarterial injection, intramuscular injection, intrasternal injection, or infusion techniques. The compounds are mixed with pharmaceutically acceptable carriers, excipients, adjuvants, and vehicles appropriate for the desired route of administration.

Oral administration is advantageous due to its ease of implementation and patient (or caretaker) compliance. In certain embodiments, the active compound and acceptable carrier are administered with a food such as cream cheese, peanut butter, or any other food with at least 25% calories from fat, to encourage uptake and absorption of the lipid-soluble quinones of the invention.

The term "nutraceutical" has been used to refer to any substance that is a food or a part of a food and provides medical or health benefits, including the prevention and treatment of disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease. Accordingly, the compounds described for use herein can also be administered as nutraceutical or nutritional formulations, with additives such as nutraceutically or nutritionally acceptable excipients, nutraceutically or nutritionally acceptable carriers, and nutraceutically or nutritionally acceptable vehicles. Such formulations are sometimes called medical foods. Suitable nutraceutically acceptable excipients may include liquid solutions such as a solution comprising one or more vegetable-derived oils, such as sesame oil, and/or one or more animal-derived oils, and/or one or more fish-derived oils. The compounds of the present invention can also be mixed with fatty food and administered as a medical food.

The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to methods known in the art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-glycerides or di-glycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents. Alternatively, the compound may also be administered in neat form if suitable.

The compounds for use in the present invention can also be administered in the form of liposomes. As is known in the art, liposomes are generally derived from phospholipids or other lipid substances. Liposomes are formed by mono or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound for use in the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

The compounds for use in the present invention can also be administered in topical, periocular, or intraocular ophthalmic formulations that additionally comprise an ophthalmically acceptable vehicle. In some embodiments the topical, periocular, or intraocular ophthalmic formulation may additionally include various other ingredients, including but not limited to surfactants, tonicity agents, buffers, preservatives, co-solvents and viscosity building agents.

The compounds and formulations for use in the present invention can also be administered using a contact lens-based bioactive agent delivery system, such as those described in U.S. Pat. Appl. Pub. No. 2009/0060981.

In one embodiment of the present invention, a topical ophthalmic formulation comprising alpha-tocotrienol quinone and an ophthalmically acceptable carrier for topical ophthalmic administration or implantation into the conjunctival sac or anterior chamber of the eye, is administered to a patient in need thereof. The formulations are formulated in accordance with methods known in the art for the particular route of administration desired.

The topical ophthalmic formulations administered topically, periocularly, or intraocularly comprise an ophthalmically effective amount of tocotrienol quinone, preferably alpha-tocotrienol quinone. As used herein, an "ophthalmically effective amount" is one which is sufficient to reduce or eliminate signs or symptoms of the ophthalmic disorders described herein. Generally, for formulations intended to be administered topically to the eye in the form of eye drops or eye ointments, the total amount of the tocotrienol quinone will be 0.001 to 1.0% (w/w). When applied as eye drops, 1-2 drops (approximately 20-45 µl each) of such formulations will be administered from once to several times per day.

The compounds of the present invention can be administered as solutions, suspensions, or emulsions (dispersions) in an ophthalmically acceptable vehicle. An "ophthalmically acceptable" component, as used herein, refers to a component which will not cause any significant ocular damage or ocular discomfort at the intended concentration and over the time of intended use. Ophthalmically acceptable components, such as solubilizers and stabilizers, should also be non-reactive with the compounds. An "ophthalmically acceptable vehicle" refers to any substance or combination of substances which are non-reactive with the compounds and suitable for administration to a patient. Suitable vehicles may be non-aqueous liquid media including the physiologically acceptable oils such as silicone oil, USP mineral oil, white oil, poly(ethyleneglycol), a polyethoxylated castor oil and vegetable oils, for example corn oil, peanut oil, or the like. Other suitable vehicles may be aqueous or oil-in-water solutions suitable for topical application to the patient's eyes. These vehicles may be preferred based on ease of formulation, as well as a patient's ability to easily administer such formulations by means of instilling one to two drops of the solutions in the affected eyes. The formulations may also be suspensions, viscous or semi-viscous gels, or other types of solid or semi-solid formulations, and fat bases, such as natural wax (e.g., white bees wax), carnauba wax, wool wax (wool fat), purified lanolin, anhydrous lanolin; petroleum wax (e.g., solid paraffin), microcrystalline wax; hydrocarbons (e.g., liquid paraffin), white petrolatum, yellow petrolatum; or combinations thereof. The formulations may be applied by use of the hands or an applicator such as a wipe, a contact lens, a dropper or a spray.

The topical ophthalmic formulations administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears, for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the formulations will have a tonicity agent in an amount sufficient to cause the final composition to have an ophthalmically acceptable osmolality (generally about 200-400 mOsm/kg).

An appropriate buffer system (e.g., sodium phosphate, sodium acetate, sodium citrate, sodium borate or boric acid) may be added to the formulations to prevent pH drift under storage conditions. The particular concentration will vary, depending on the agent employed. Preferably, however, the buffer will be chosen to maintain a target pH within the range of pH 6-7.5.

Topical ophthalmic formulations for the treatment of ophthalmic disorders associated with LHON and DOA may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous formulations which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more of the compounds disclosed herein. Examples of artificial tears compositions useful as artificial tears carriers include, but are not limited to, commercial products, such as Tears Naturale®, Tears Naturale II®, Tears Naturale Free®, and Bion Tears® (Alcon Laboratories, Inc., Fort Worth, Tex.). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers in the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as glycerol, propylene glycol, ethylene glycol; polymeric polyols, such as polyethylene glycol, hydroxypropylmethyl cellulose, carboxy methyl cellulose sodium, hydroxypropyl cellulose; dextrans, such as dextran 70; water soluble proteins, such as gelatin; and vinyl polymers, such as polyvinyl alcohol, polyvinylpyrrolidone, povidone and carbomers.

Other compounds may also be added to the topical ophthalmic formulations of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The tocotrienol quinones of the present invention can also be administered via periocular administration, and may be formulated in solutions or suspensions for periocular administration. Formulations useful for periocular administration will generally be periocular injection formulations or surgical irrigating solutions. Periocular administration refers to administration to tissues near the eye, such as administration to the tissues or spaces surrounding the eyeball and within the orbit. Periocular administration can take place by injection, deposit, or any other mode of placement. Periocular routes of administration include, but are not limited to, subconjunctival, suprachoroidal, juxtascleral, posterior juxtascleral, sub-Tenon, posterior sub-Tenon, retrobulbar, peribulbar, or laterobulbar delivery. Raghava et al., Expert Opin. Drug Deliv. 1(1):99-114 (2004); Ghate et al. Investigative Ophthalmology and Visual Science, 48 (5): 2230 (2007); Karl G. Csaky, Retina Today, pp. 32-35 (March/April 2007); WO 2009/023877; and EP 1611879 describe various routes of periocular administration.

The tocotrienol quinones of the present invention may be formulated in solutions or suspensions for intraocular administration. Formulations useful for intraocular administration will generally be intraocular injection formulations or surgical irrigating solutions.

In general, the doses utilized for the above described purposes will vary, but will be in an effective amount to prevent, reduce or ameliorate LHON or DOA. As used herein, "ophthalmically effective amount" or "therapeutically effective amount" refers to that amount of active agent which prevents, reduces or ameliorates LHON or DOA. The tocotrienol quinones will generally be contained in the topical, periocular, or intraocular formulations contemplated herein in an amount of from about 0.001 to about 10.0% weight/volume ("% w/v"). Preferred concentrations will range from about 0.1 to about 5.0% w/v. Topical formulations will generally be delivered to the eye one to six times a day, at the discretion of a skilled clinician.

The amount of active ingredient that may be combined with the carrier materials to produce a single dosage form can vary depending upon the patient to which the active ingredient is administered and the particular mode of administration. It will be understood, however, that the specific dose level for any particular patient will depend upon a variety of factors including the activity of the specific compound employed; the age, body weight, body area, body mass index (BMI), general health, sex, and diet of the patient; the time of administration and route of administration used; the rate of excretion; drug combination, if any, used; and the progression and severity of the disease in the patient undergoing therapy. The pharmaceutical unit dosage chosen is usually fabricated and administered to provide a defined final concentration of drug in the blood, retina, or other targeted region of the body.

Compounds for use in the present invention may be administered in a single daily dose, or the total daily dosage may be administered in divided dosages of two, three or four times daily.

While the compounds for use in the present invention can be administered as the sole active pharmaceutical agent, they can also be used in combination with one or more other agents used in the treatment or suppression of disorders.

When additional active agents are used in combination with the compounds for use in the present invention, the additional active agents may generally be employed in therapeutic amounts as indicated in the Physicians' Desk Reference (PDR) 63rd Edition (2009), which is incorporated herein by reference, or such therapeutically useful amounts as would be known to one of ordinary skill in the art, or as are determined empirically for each patient.

The compounds for use in the present invention and the other therapeutically active agents can be administered at the recommended maximum clinical dosage or at lower doses. Dosage levels of the active compounds in the compositions for use in the present invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

In one embodiment, the purity of the preparation of the compound, such as a tocotrienol quinone preparation, is measured prior to the addition of any pharmaceutical carriers or excipients, or any additional active agents. For example, if alpha-tocotrienol quinone is prepared according to any of the methods described in International Patent Application No. PCT/US2009/062212 or U.S. patent application Ser. No. 12/606,923, the purity of the alpha-tocotrienol quinone is measured on the final product of the method selected, and prior to adding the pharmaceutical carrier(s) or excipient(s) or additional active agent(s). The purity of the desired tocotrienol quinone, or other compound, by weight, can be at least about 20%, at least about 30%, at least about 40%, at least about 50%, at least about 60%, at least about 70%, at least about 75%, at least about 80%, at least about 85%, at least about 90%, at least about 95%, at least about 96%, at least about 97%, at least about 98%, or at least about 99%, prior to the addition of any pharmaceutical carriers or excipients, or any additional active agents. These same numerical purity levels can also be used as by mole fraction, or by any other relative measurement (such as weight/volume).

In another embodiment, the purity of the preparation of the compound, such as a tocotrienol quinone preparation, is measured as a fraction of the desired tocotrienol quinone relative to the total amount of tocotrienol quinones and (if present) tocotrienols in the preparation. For example, a composition containing 100 mg of alpha-tocotrienol quinone, 50 mg of beta-tocotrienol quinone, and 50 mg of gamma-tocotrienol hydroquinone would be described as 50% alpha tocotrienol quinone by weight, irrespective of the amounts of other non-tocotrienol or non-tocotrienol quinone compounds present in the preparation. This measurement of purity would be the same whether measured before or after addition of pharmaceutical carriers or excipients, or before or after addition of any non-tocotrienol/non-tocotrienol quinone active agents. The purity of the desired tocotrienol quinone, or other compound, by weight, can be at least about 20%, at least about 30%, at least about 40%, at least about 50%, at least about 60%, at least about 70%, at least about 75%, at least about 80%, at least about 85%, at least about 90%, at least about 95%, at least about 96%, at least about 97%, at least about 98%, or at least about 99%. These same numerical purity levels can also be used as by mole fraction, or by any other relative measurement (such as weight/volume).

Kits

The invention also provides articles of manufacture and kits containing materials useful for treating LHON and DOA. The article of manufacture comprises a container with a label. Suitable containers include, for example, bottles, vials, and test tubes. The containers may be formed from a variety of materials such as glass or plastic. The container holds a compound selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or a composition comprising an active agent selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone. In one embodiment, the compound is alpha-tocotrienol quinone. In one embodiment, the active agent is alpha-tocotrienol quinone. The label on the container indicates that the composition is used for treating LHON and DOA, and may also indicate directions for use in treatment.

The invention also provides kits comprising any one or more of a compound selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or a composition comprising an active agent selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone. In some embodiments, the kit of the invention comprises the container described above, which holds a compound selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or a composition comprising an active agent selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone. In other embodiments, the kit of the invention comprises the container described above, which holds a compound selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or a composition comprising an active agent selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, and a second container comprising a vehicle for the compound or composition, such as one or more vegetable-derived oils, such as sesame oil, and/or one or more animal-derived oils, and/or one or more fish-derived oils. In other embodiments, the kit of the invention comprises the container described above, which holds a compound selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, or a composition comprising an active agent selected from alpha-tocotrienol quinone, beta-tocotrienol quinone, gamma-tocotrienol quinone, delta-tocotrienol quinone, alpha-tocotrienol hydroquinone, beta-tocotrienol hydroquinone, gamma-tocotrienol hydroquinone, and delta-tocotrienol hydroquinone, where the compound or composition has been pre-mixed with a vehicle for the compound or composition, such as one or more vegetable-derived oils, such as sesame oil, and/or one or more animal-derived oils, and/or one or more fish-derived oils. The kits may further include other materials desirable from a commercial and user standpoint, including other vehicles, buffers, diluents, filters, needles, syringes, and package inserts with instructions for performing any of the methods described herein for treatment of LHON or DOA.

In other aspects, the kits may be used for any of the methods described herein, including, for example, to treat an individual with LHON or DOA.

EXAMPLES

Example 1

LHON Cell Line Assay and Initial Screen for Effective Compounds

Alpha-Tocotrienol quinone was tested for its ability to rescue Leber's Hereditary Optic Neuropathy (LHON) fibroblast cells obtained from the Coriell Cell Repositories (Camden, N.J.; repository number GM03858), from stress effected by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. EC50 concentrations of test compound and its redox-silent version were determined and compared.

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, and insulin from bovine pancreas were purchased from Sigma. Calcein AM was purchased from Molecular Probes. Cell culture medium was made by combining 125 mL M199 EBS, 50 ml Fetal Calf Serum, 100 U/mL penicillin, 100 µg/ml streptomycin, 2 mM glutamine, 10 µg/mL insulin, 10 ng/mL EGF, and 10 ng/mL bFGF. MEM EBS was added to make the volume up to 500 mL. A 10 mM BSO solution was prepared by dissolving 444 mg BSO in 200 mL of medium with subsequent filter-sterilization. During the course of the experiments, this solution was stored at +4° C.

The test samples were supplied in 1.5 mL glass vials. The compounds were diluted with DMSO, ethanol or PBS to result in a 5 mM stock solution. Once dissolved, they were stored at −20° C.

Test samples were screened according to the following protocol: A culture with LHON fibroblasts was started from a 1 mL vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 mL medium, corresponding to 100 µL medium with 3,000 cells/well. The remaining cells were distributed in 10 cm cell culture plates (500,000 cells/plate) for propagation. The plates were incubated overnight at 37° C. in an atmosphere with 95% humidity and 5% $CO_2$ to allow attachment of the cells to the culture plate.

MTP medium (243 µL) was added to a well of the microtiter plate. The test compounds were unfrozen, and 7.5 µL of a 5 mM stock solution was dissolved in the well containing 243 µL medium, resulting in a 150 µM master solution. Serial dilutions from the master solution were made. The period between the single dilution steps was kept as short as possible (generally less than 1 second).

Plates were kept overnight in the cell culture incubator. The next day, 10 µL of a 10 mM BSO solution were added to the wells, resulting in a 1 mM final BSO concentration. Forty-eight hours later, three plates were examined under a phase-contrast microscope to verify that the cells in the 0% control (wells E1-H1) were clearly dead. The medium from all plates was discarded, and the remaining liquid was removed by gently tapping the plate inversed onto a paper towel.

100 µL of PBS containing 1.2 µM Calcein AM were then added to each well. The plates were incubated for 50-70 minutes at room temperature. After that time the PBS was discarded, the plate gently tapped on a paper towel and fluorescence (excitation/emission wavelengths of 485 nm and 525 nm, respectively) was read on a Gemini fluorescence reader. Data was imported into Microsoft Excel (EXCEL is a registered trademark of Microsoft Corporation for a spreadsheet program) and used to calculate the $EC_{50}$ concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). The compounds showed no auto-fluorescence. The viability of non-BSO treated fibroblasts was set as 100%, and the viability of the BSO- and compound-treated cells was calculated as relative to this value.

The results of the cell viability assay for the LHON-mutant cells in the presence of alpha-tocotrienol quinone (αTTQ) are shown in FIG. 1. Alpha-tocotrienol quinone protects the cells with an $ED_{50}$ of 12 nM.

Example 2

Treatment of a Female LHON Patient (A) Diagnosed with a LHON Mutation

A fifty two-year-old female patient (A) with a LHON 11778 point mutation was treated with alpha-tocotrienol quinone. Patient (A) also suffered from retinopathy in her left eye when treatment was started.

Alpha-tocotrienol quinone was administered to the patient orally; the drug was mixed with sesame oil for administration, and the intake was taken with ice-cream. The following dosing of alpha-tocotrienol quinone was used:

On Day 1 the dose was 100 mg TID. It was escalated on Day 8 to 200 mg TID and continued at this dosage.

While being treated with alpha tocotrienol quinone, the patient's medical team monitored the patient's eyes for any signs of improvement or signs of worsening of the disease.

The following results, shown in FIGS. 2, 3, 4, and 5, were obtained: (i) absence of loss of visual acuity progression and improvement from 20/400 to 20/200; (ii) no change in color vision, (iii) improvement in visual field and stable OCT.

Close monitoring of patient (A) during the study was performed, to detect any adverse events. In addition, the investigator had authority to stop the study if the safety of the subject was at risk. No adverse events were observed.

Example 3

Treatment of a Male LHON Patient (B) Diagnosed with a LHON Mutation

A 23-year-old male patient (B) with a LHON 11778 point mutation was treated with alpha-tocotrienol quinone. At the beginning of treatment the visual acuity was 20/400 for the right eye and 20/200 for the left eye. As for Patient (A), Patient (B) was treated with a 100 mg TID for seven days and the dose was escalated to 200 mg TID on day 8.

FIGS. 6, 7, 8 and 9 show the results obtained during the first two months of treatment: (i) absence of loss of visual acuity progression and improvement on right eye from 20/400 to 20/200 and improvement on left eye from 20/200 to 20/100; (ii) improvement of color vision in his right eye and maintenance of color vision in his left eye; (iii) improvement in visual fields, and (iv) stable OCT in the left eye.

Close monitoring of Patient (B) during the study was performed, to detect any adverse events. In addition, the investigator had authority to stop the study if the safety of the subject was at risk. No adverse events were observed.

Patient (B) was able to return to work, and continued his intake of 200 mg/tid alpha-tocotrienol quinone.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A method of treating dominant optic atrophy (DOA) in an individual, comprising administering a therapeutically effective amount of a compound selected from the group consisting of alpha-tocotrienol quinone, beta-tocotrienol quinone, gamma-tocotrienol quinone, delta-tocotrienol quinone, and the corresponding hydroquinones thereof, to an individual suffering from dominant optic atrophy (DOA).

2. The method of claim 1, wherein the compound is selected from the group consisting of alpha-tocotrienol quinone, beta-tocotrienol quinone, gamma-tocotrienol quinone, and delta-tocotrienol quinone.

3. The method of claim 1, wherein the compound is selected from the group consisting of alpha-tocotrienol hydroquinone, beta-tocotrienol hydroquinone, gamma-tocotrienol hydroquinone, and delta-tocotrienol hydroquinone.

4. The method of claim 2, wherein the compound is alpha-tocotrienol quinone.

5. The method of claim 1, wherein the individual suffering from DOA has at least one mutation of at least one OPA gene selected from the group consisting of OPA1, OPA2, OPA3, OPA4, OPA5, OPA6 and OPA7.

6. The method of claim 1, wherein the individual suffering from DOA has at least one mutation in at least the OPA1 gene.

7. The method of claim 1, wherein the individual has one or more symptoms selected from the group consisting of: loss of visual acuity, loss of central vision, impairment of color vision, centrocecal scotomas, temporal pallor of the optic disc, circumpapillary telangiectatic microangiopathy, sparing of pupillary light responses, swelling of the retinal nerve fiber layer around the disc (pseudoedema), and optic atrophy.

8. The method of claim 4, comprising administering a pharmaceutical preparation containing from 50 mg to 500 mg of alpha-tocotrienol quinone.

9. The method of claim 4, comprising administering a pharmaceutical preparation containing sufficient alpha-tocotrienol quinone to provide a therapeutic level of compound in at least the retina or the optic nerve system of the individual.

10. The method of claim 8, wherein the alpha-tocotrienol quinone comprises at least 50% by weight of the tocotrienols and tocotrienol quinones present in the preparation.

11. The method of claim 10, wherein the alpha-tocotrienol quinone comprises at least 80% by weight of the material present in the preparation, excluding the weight of any added pharmaceutical carriers or excipients.

12. The method of claim 4, comprising administering the alpha-tocotrienol quinone as a unit dosage formulation of alpha-tocotrienol quinone, wherein the alpha-tocotrienol quinone comprises at least 95% by weight of the tocotrienols and tocotrienol quinones present in the unit dosage formulation.

13. The method of claim 8, wherein the individual has one or more symptoms selected from the group consisting of: loss of visual acuity, loss of central vision, impairment of color vision, centrocecal scotomas, temporal pallor of the optic disc, circumpapillary telangiectatic microangiopathy, sparing of pupillary light responses, swelling of the retinal nerve fiber layer around the disc (pseudoedema), and optic atrophy.

14. The method of claim 8, wherein the preparation is administered via topical, periocular, or intraocular administration.

15. The method of claim 8, wherein the preparation is administered via oral administration.

16. The method of claim 3, wherein the compound is alpha-tocotrienol hydroquinone.

* * * * *